United States Patent
Marcus et al.

(10) Patent No.: US 6,852,969 B2
(45) Date of Patent: *Feb. 8, 2005

(54) ATMOSPHERIC PRESSURE, GLOW DISCHARGE, OPTICAL EMISSION SOURCE FOR THE DIRECT SAMPLING OF LIQUID MEDIA

(75) Inventors: R. Kenneth Marcus, Seneca, SC (US); W. Clay Davis, Charleston, SC (US)

(73) Assignee: Clemson University, Clemson, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 10/636,177

(22) Filed: Aug. 7, 2003

(65) Prior Publication Data

US 2004/0026616 A1 Feb. 12, 2004

Related U.S. Application Data

(63) Continuation-in-part of application No. 10/622,187, filed on Jul. 17, 2003, which is a continuation of application No. PCT/US02/01523, filed on Jan. 17, 2002.
(60) Provisional application No. 60/264,888, filed on Jan. 29, 2001.

(51) Int. Cl.[7] .......................... H01J 49/10; G01N 21/69
(52) U.S. Cl. ...................... 250/288; 250/281; 250/282; 250/306; 250/307; 356/316; 315/111.01; 315/111.21
(58) Field of Search ................................ 250/288, 281, 250/282, 306, 307; 315/111.01, 111.21; 356/316

(56) References Cited

U.S. PATENT DOCUMENTS 6,686,998 B2 * 2/2004 Gianchandani et al. ...... 356/316

OTHER PUBLICATIONS

Glow Discharge Spectra of Copper and Indium Above Aqueous Solutions, Dwight E. Couch and Abner Brenner, Chemistry Division, National Bureau of Standards, Washington, D.C., pp. 628 and 629.

Emission Studies on a Glow Discharge in Atmospheric Pressure Air Using Water as a Cathode, T. Cserfaivi, P. Mezei and P. Apai, J. Phys. D. Appl. Phys. 26 (1993) pp. 2184–2188.

(List continued on next page.)

*Primary Examiner*—Nikita Wells
(74) *Attorney, Agent, or Firm*—Dority & Manning, P.A.

(57) ABSTRACT

A glow discharge spectroscopy (GDS) source operates at atmospheric pressure. One of the discharge electrodes of the device is formed by an electrolytic solution 27 containing the analyte specimen. The passage of electrical current (either electrons or positive ions) across the solution/gas phase interface causes local heating and the volatilization of the analyte species. Collisions in the discharge region immediately above the surface of the solution results in optical emission and ionization that are characteristic of the analyte elements. As such, these analyte elements can be identified and quantified by optical emission spectroscopy (OES) or mass spectrometry (MS). The device uses the analyte solution as either the cathode or anode. Operating parameters depend on the electrolyte concentration (i.e. solution conductivity) and the gap 35 between the solution surface and the counter electrode. Typical conditions include discharge currents of about 10 to about 60 mA and potentials of about 200 to about 1000 volts. Electrolyte solutions of pH, pNa or pLi values of about 0.5 to about 2 and inter-electrode gaps of about 0.5 to about 3 mm produce stable plasmas where the analyte solutions are totally consumed at flow rates of up to about 2.0 mL/min.

42 Claims, 21 Drawing Sheets

OTHER PUBLICATIONS

Direct Solution Analysis by Glow Discharge: Electrolyte–Cathode Discharge Spectrometry, Tamas Cserfaivi, Pal Mezei, Journal of Analytical Atomic Spectrometry, Mar. 1994, vol. 9, pp. 346–349.

Pressure Dependence of the Atmospheric Electrolyte Cathode Glow Discharge Spectrum, Pal Mezei, Tamas Cserfaivi and Mihaly Janossy; Journal of Analytical Atomic Spectrometry (1997), pp. 1203–1208.

Rapid Communication the Gas Temperature in the Cathode Surface—Dark Space Boundary Layer of an Electrolyte Cathode Atmospheric Glow Discharge (ELCAD), P. Mezei, T. Cserfaivi, and M. Janossy; J. Phys. D: Appl. Phys. 31 (1998) pp. L41–L42.

Fundamental Studies of Electrolyte–as–Cathode Glow Discharge–Atomic Emission Spectrometry for the Determination of Trace Metals in Flowing Water, Yang S. Park, Soo H. Ku, Sung H. Hong, Hyo J. Kim and Edward J. Piepmeier; Spectrochimica Acta Part B 53 (1998), pp. 1167–1179.

Development of Open–Air Type Electrolyte–as–Cathode Glow Discharge—Atomic Emission Spectrometry for Determination of Trace Metals in Water, Hyo J. Kim, Jeong H. Lee, Myung Y. Kim, T. Cserfaivi and P. Mezei; Sectrochimica Acta Part B 55 (2000) pp. 823–831.

A Brief Overview of the Present Status of the Mechanisms Involved in Electrospray Mass Spectrometry, P. Kebarle, J. Mass Spectrom. 35, pp. 804–817 (2000).

Downsizing Chemistry Chemical analysis and synthesis on microchips promise a variety of potential benefits, Michael Freemantle, C&EN London, Feb. 22, 1999, pp. 27–36.

* cited by examiner

ANALYTICAL RESPONSE FUNCTIONS AND LIMITS OF DETECTION FOR THE LS-APGD DEVICE. SOLUTION FLOW RATE = 1 mL/MIN., ELECTROLYTE pH = 1, INTER ELECTRODE GAP = 1 mm, INJECTION VOLUME = 5μL.

| ELEMENT | WAVELENGTH (nm) | PEAK HEIGHT EQN. | $R^2$ | PEAK AREA EQN. | $R^2$ | LOD ppm (ng) |
|---|---|---|---|---|---|---|
| Na | 589.0 | Y=0.421x + 42.8 | 0.9859 | Y=15.81x + 978.6 | 0.9784 | 12 (60) |
| Fe | 248.3 | Y=1.06x - 102.1 | 0.9365 | Y=45.80x - 6649 | 0.909 | 12 (60) |
| Pb | 405.8 | Y=1.18x - 10.45 | 0.977 | Y=16.16x - 419.7 | 0.9298 | 14 (70) |

*Fig. 10*

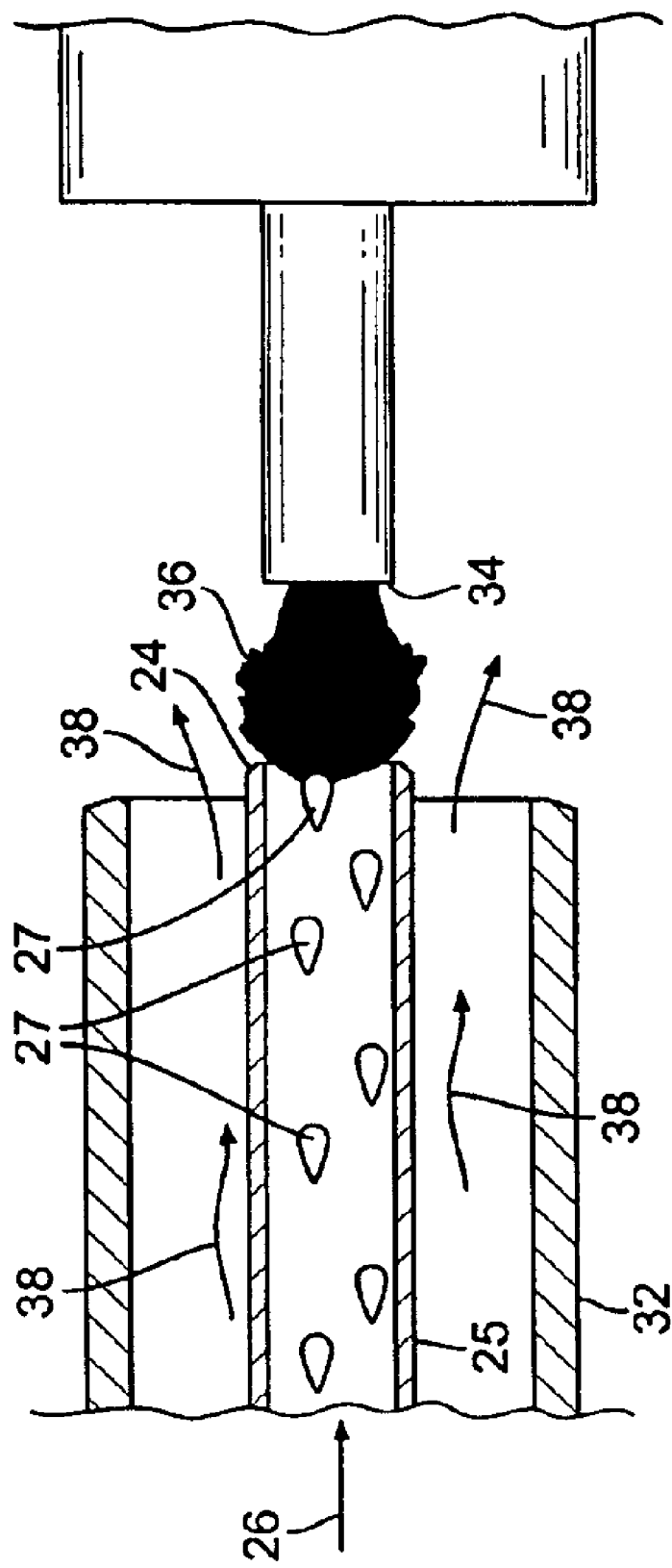

ATMOSPHERIC PRESSURE, GLOW DISCHARGE, OPTICAL EMISSION SOURCE FOR THE DIRECT SAMPLING OF LIQUID MEDIA

CROSS-REFERENCE TO RELATED APPLICATIONS

This application is a continuation-in-part to U.S. application Ser. No. 10/622,187, filed Jul. 17, 2003, which is a continuation of PCT International Application Serial No. PCT/US02/01523 filed Jan. 17, 2002, which is a continuation of U.S. Provisional Application Ser. No. 60/264,888 filed Jan. 29, 2001.

FEDERALLY SPONSORED RESEARCH

Not applicable.

BACKGROUND OF THE INVENTION

The present invention relates to spectrochemical sources and more particularly to glow discharge sources.

Glow discharge (GD) plasmas have been used as spectrochemical (i.e., optical emission) sources for well over 100 years, dating back to the early studies of atomic structure. The low pressure, low power plasmas are easily controlled and yield emission spectra that are principally atomic in nature. The combination of cathodic sputtering as a means of introducing atoms from bulk solids and the relatively simple optical spectra lead to the implementation of hollow cathode GD devices as line sources for atomic absorption spectrophotometry. The development of the Grimm-type glow discharge geometry lead to the use of glow discharge optical emission spectroscopy (GD-OES) as a tool for both bulk solid and depth resolved analysis of metals and alloys. The subsequent introduction of radio frequency (rf) powering schemes opened up the scope of application further to nonconductive materials and coatings.

One of the strongest features of standard glow discharge devices is the fact that they operate in inert environments and are thus free from atmospheric contaminants. While the cathodic sputtering event entails sufficient energy to release neutral atoms and molecules from solid matrices, the discharge's gas phase temperature is insufficient to cause desolvation of analytes introduced in water vapor, a phenomenon that is typical in atmospheric pressure flames and plasmas. As such, a good deal of effort has been devoted to developing strategies for getting liquid-originating analytes into the discharge environment.

The most common method for getting liquid-originating analytes into the discharge environment involves drying an aliquot of analyte-containing solution on an inert target that is subsequently introduced as the cathode of the GD source so that the dried residue can be sputtered from the cathode's surface. In this way, solvent vapors are excluded from the discharge volume, and the plasma operated much in its "normal" manner. While effective, this approach is laborious and not amenable to what would ideally be the analysis of flowing streams such as liquid chromatograph eluents. To address this shortcoming, transport-type liquid chromatography-mass spectrometry (LC-MS) interfaces such as the moving belt and the particle beam have been used to introduce dried analytes into the plasmas in a continuous fashion. Schroeder and Horlick have also attempted to introduce nebulized solutions directly into a hollow cathode emission source with some level of success.

Over 40 years ago, Couch and Brenner described a phenomenon by which a glow discharge plasma was sustained at atmospheric pressure between a tungsten anode and an electrolyte solution that acted as the cathode. Solutions containing copper and indium dopants produced optical emission spectra analogous to that obtained in flame emission sources. On the other hand, solutions containing other cationic species (Li, Na, S, and U) did not yield characteristic spectra. The Couch/Brenner device was actually a modified version of a system that originally was described by Gubkin and later reviewed by Hickling and Linacre and was employed for very high yield electrolysis of aqueous solutions of metal salts.

Cserfalvi and co-workers reinvestigated this phenomenon as a means of analyzing dissolved metals in electrolytic solutions, coining the term electrolyte-cathode discharge (ELCAD). In their original apparatus, the electrolyte-containing solution was disposed in a basin having two regions separated by a glass frit. A graphite rod that was electrically maintained at the cathodic potential of the discharge circuit was submerged in one of the regions of the basin. A central inlet tube passed vertically through the other region of the basin. The analyte-containing solution was continuously re-circulated at flow rates of 2 to 10 milliliters per minute (mL/min) through the central inlet tube so as to form a small stationary "waterfall" with a slope of about 60 degrees at the edge of the central inlet tube. A tungsten electrode (acting as the anode) was mounted one to five millimeters (mm) above this slope of the waterfall. The glow discharge formed in the space between the end of the anode and the slope of the waterfall. The glass frit separated the region of the basin containing the waterfall from the region containing the cathode rod in order to eliminate the evolution of $H_2$ gas and possible explosion. Current-voltage (i-V) plots generated for that device supported the assumption that the devices did indeed operate in the so-called "abnormal" glow discharge regime. Both operating voltage and observed analyte emission responses were dependent on the pH of the test solutions, with the authors suggesting that solution conductivity, and more specifically hydronium ion concentration, being a key aspect of the physical operation of the devices. Detection limits for more or less bulk solutions of metal analytes produced detection limits of approximately 0.1 to 1 part per million (ppm), though for total analyte solution volumes of more than 10 milliliters (mL).

Subsequent studies on the ELCAD source by Mezei, Cserfalvi, and Jánossy, sought to elucidate the operating mechanism of the device. The authors used a variable pressure cell to study the role of gas-phase collision frequency on the operating characteristics. In most cases, increases in gas (atmosphere) pressure from 500 to 1200 millibar (mbar) yielded greater emission intensities, which the authors ascribed to increased three-body recombination of analyte ions sputtered from the solution surface (i.e., $M^+ + e + e \text{---} M^* + e$). Neutralized atoms in the analytes could then in turn be excited in the plasma region immediately above the surface of the solution. Based on the known field structure in the vicinity of the cathode electrode in a glow discharge, the actual release of a cationic species from the surface of the solution seems very unlikely. The authors subsequently calculated a gas-phase temperature above the cathode surface based on an assumption of the kinetic energy of ions colliding with the liquid surface. A gas-phase temperature of approximately 7000 degrees Kelvin was suggested.

Kim and co-workers have recently described an extension of the studies of Mezei et al. by the use of an ELCAD system wherein argon is introduced as the discharge gas in a pseudo-closed vessel system that was purged through a bubbler. In their design, a platinum wire anode was placed opposite the analyte "waterfall" with analyte flow rates of 5 to 10 mL/min. The Ar gas served to also reduce the possibility of explosion, and the high solution flow rates kept the sample solution from boiling. This group performed parametric studies of the sorts described above, finding as well that the current-voltage (i-V) characteristics of the plasma were representative of an abnormal glow discharge with dependencies on both the pH of the solution and the inter-electrode gap. Interestingly, the authors observed no emission from the Ar discharge gas species, though in the wavelength range investigated (400–500 nm) only Ar (II) species would be expected to be present. Here too, the authors proposed a mechanism whereby ions of the analyte metals were sputtered from the solution (cathode) surface, subsequently neutralized in the cathode dark space and then excited within the plasma, with the parametric dependencies indicating that some sort of sputtering threshold must be realized prior to analyte release. Analyte emission intensities were found to come to steady state conditions following one minute of introduction at flow rates of 10 mL/min. Once stabilized, analyte stabilities of approximately 2.5% relative standard deviation (RSD) were obtained. Limits of detection (LOD) were subsequently calculated to be in the 0.001 to 1 ppm range.

Kim et al extended their work to an open-air cell that connected the cathode to the water in the cell by a platinum wire. The liquid sample was introduced through a peristaltic pump and flowed over the cathode. It was found that the surface tension of the sample solution made it difficult to maintain continuous flow over the cathode at flow rates lower than 5 mL/min. It also was found that maintaining the flow rate above 5 mL/min helped prevent the sample from boiling. This work yielded similar operating characteristics to the prior work of Kim et al, though the analytical performance of the open-air cell was degraded both as to the time required to reach the steady state (2 to 3 mins.) and the precision (less than 8.7% RSD in time and 2.9% for repetitive wavelength scans) of the analysis. Improvements in LODs of as much as one order of magnitude were observed for some transition metal elements, with values of 0.01 to 0.03 ppm being typical.

OBJECTS AND SUMMARY OF THE INVENTION

It is a principal object of the present invention to provide apparatus and method that can analyze aqueous streams directly under atmospheric conditions by the use of a low power (less than 200 Watts) dc plasma.

It is another principal object of the present invention to provide apparatus and method that can analyze aqueous streams directly under atmospheric conditions by the use of a low power (less than 200 W) dc plasma in sample-limited (flow injection) applications.

It is a further principal object of the present invention to provide apparatus and method that can analyze aqueous streams directly under atmospheric conditions by the use of a low power (less than 200 W) dc plasma in chromatographic applications.

It is yet another principal object of the present invention to provide apparatus and method that can analyze aqueous streams directly under atmospheric conditions by the use of a low power (less than 200 W) dc plasma in applications that are both sample-limited (flow injection) and chromatographic.

It is a still another principal object of the present invention to provide apparatus and method that can analyze aqueous streams directly under atmospheric conditions by the use of a low power (less than 200 W) dc plasma without the high analyte solution flow rates (5 to 10 mL/min) of conventional devices and methods.

It is a still further principal object of the present invention to provide apparatus and method that can analyze aqueous streams directly under atmospheric conditions by the use of a low power (less than 200 W) dc plasma without the long stabilization period (1 to 3 mins.) upon analyte introduction of conventional devices and methods.

It is yet a further principal object of the present invention to provide apparatus and method that can analyze aqueous streams directly under atmospheric conditions by the use of a low power (less than 200 W) dc plasma without either the high analyte solution flow rates (5 to 10 mL/min) or long stabilization period (1 to 3 mins.) upon analyte introduction of conventional devices and methods.

In one embodiment, the present invention includes a new liquid sampling-atmospheric pressure glow discharge (LS-APGD) optical emission source for the direct analysis of metals and non-metals in electrolytic solutions. A hollow capillary can have an electrically conducting element that electrically communicates with the interior of the capillary and thus with the electrolyte fluid passing through the capillary. The capillary has an inlet end and a discharge end disposed opposite to the inlet end. In some embodiments, the discharge end of the capillary can be formed of metal, and in other embodiments the discharge end of the capillary can be formed of material that is electrically insulating or semiconducting. A mechanism is provided to move the electrolytic solution through the capillary at rates in the range of about $1.0 \times 10^{-6}$ l/min to about 5 milliliters/min at atmospheric pressure. A counter-electrode is fixed to a movable stage and is disposed at a predetermined distance from the discharge end of the capillary. This predetermined distance defines an electrode gap and is typically in the range of about 0.1 mm to about 5 mm. An electrical power source is electrically connected between the electrically conducting element of the capillary and the counter-electrode so that a potential difference can be placed between the counter-electrode and the electrically conducting element of the capillary. When an electrolyte solution is pumped through the capillary, a plasma whose i-V characteristics are within the range of conventional, abnormal glow discharges operating in the 0.1 to 10 Torr pressure regime is created. The discharge end of the capillary can be surrounded by a cylinder that carries a flow of gas such as nitrogen that cools the discharge end and shapes the glow discharge. An injector can be connected in fluid communication with the capillary for introducing into the electrolyte solution flowing through the capillary, fluid that contains samples of analyte, i.e., materials to be analyzed.

In one illustrative embodiment, the glow discharge plasma is initiated at the surface of the solution as the solution passes from a 0.254 mm inside diameter stainless steel tube at solution flow rates of 1 to 3 mL/min. The discharge shows abnormal discharge behavior, with the operating voltage being dependent on the pH/pLi/pNa of the solution and the inter-electrode gap. The LS-APGD runs stably at rates of $1 \times 10^{-6}$ l/min and above and also permits the direct introduction into the flow of the electrolyte solution, an injection of analyte into that electrolyte solution. In some embodiments of the present invention, an injector is connected in fluid communication with the capillary so that the sample can be introduced in a flow injection mode, with sample volumes as small as about $5 \times 10^{-6}$ liters injections. Discharge currents of 10 to 60 mA and potentials of 200 to 1000 volts are typical. Analytical response curves were generated for the elements Na, Fe, and Pb, with absolute limits of detection on the order of 60 ng obtained for 5 µL sample injections. Contrary to the cited prior art ELCAD devices, the apparatus and method of the present invention permits the operator to use the solution as either the cathode or the anode of the glow discharge.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 10 is a chart of analytical response functions and limits of detection for an embodiment of the LS-APGD device of the present invention.

FIG. 14 is an expanded view of a portion taken from FIG. 13.

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. The same numerals are assigned to the same components throughout the drawings and description.

Figure 11:
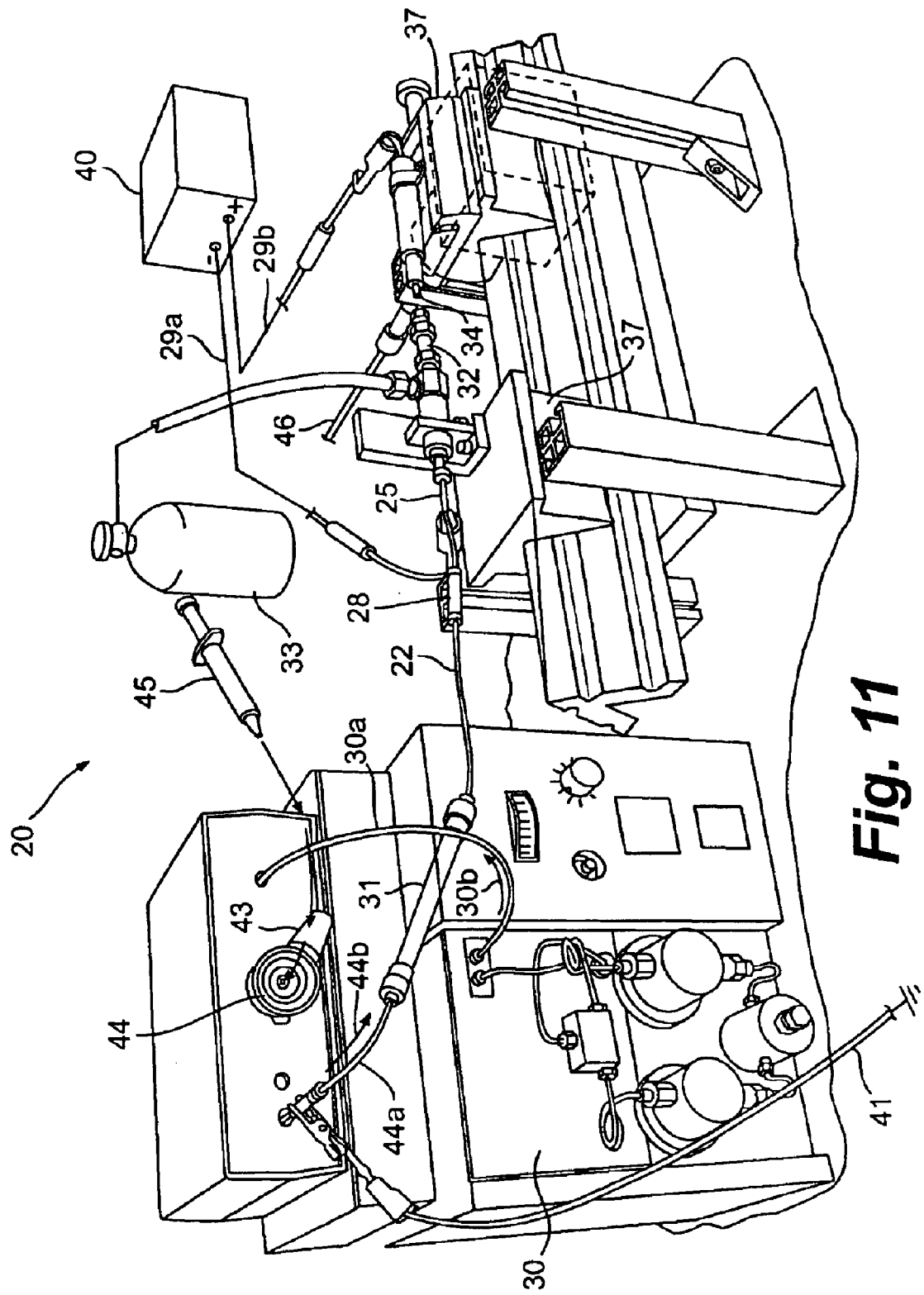
FIG. 11 is a diagrammatic representation of an embodiment of the liquid sampling-atmospheric pressure glow discharge (LS-APGD) apparatus of the present invention.
Figure 12:
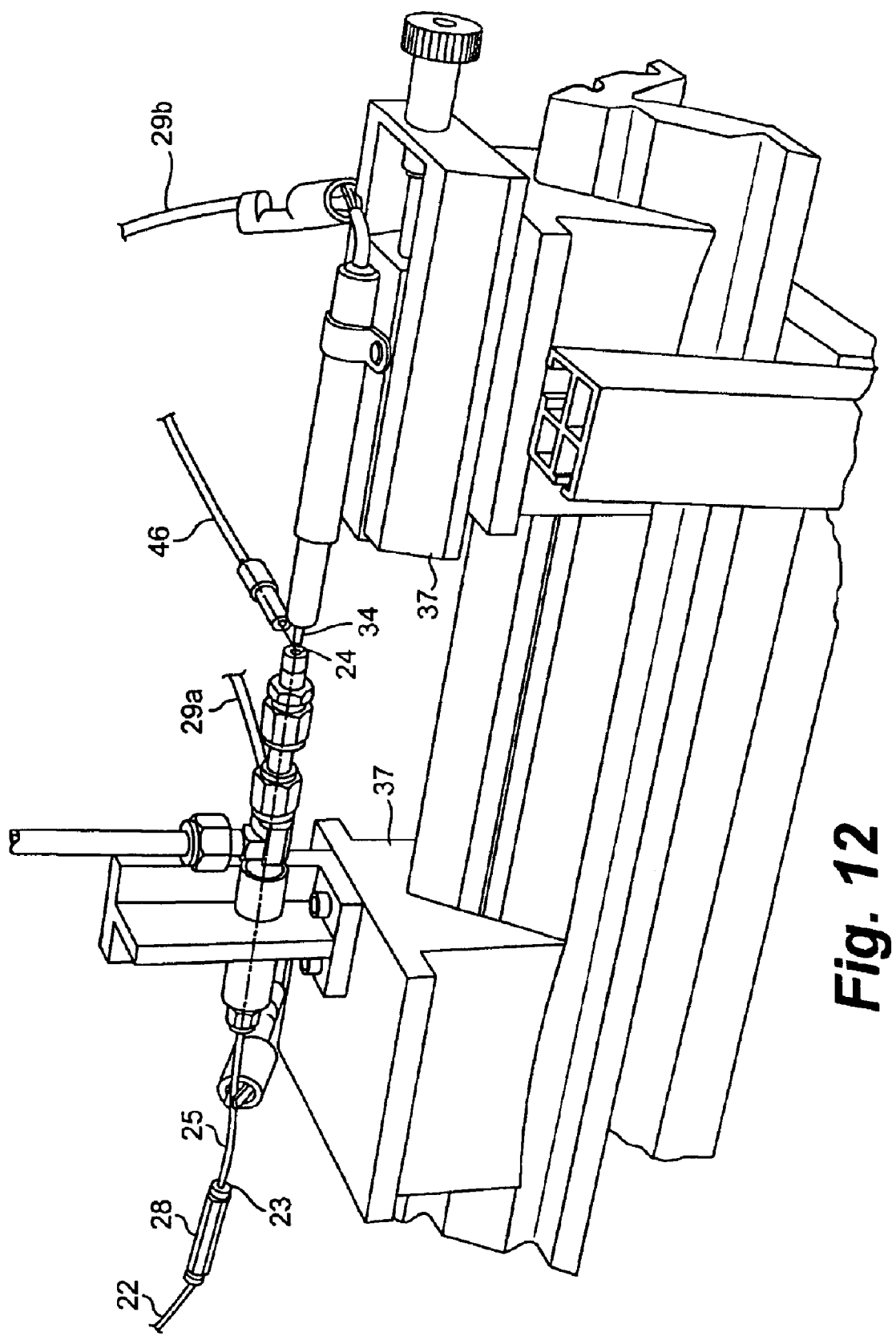
FIG. 12 is an expanded view of a portion taken from FIG. 11.

A presently preferred embodiment of the liquid sampling-atmospheric pressure glow discharge (LS-APGD) apparatus of the present invention is shown in FIGS. 11–14 and is represented generally in FIG. 11 by the numeral 20. As shown in FIG. 12 for example, the liquid sampling-atmospheric pressure glow discharge (LS-APGD) apparatus of the present invention includes a hollow capillary 22 that has an electrically conducting element such as a metallic section 25 and an inlet end 23 and a discharge end 24 disposed opposite to the inlet end. The LS-APGD includes a mechanism for moving an electrolytic solution through the capillary and past the electrically conducting element so as to be expelled from the discharge end of the capillary at rates in the range of about $1.0 \times 10^{-6}$ l/min to about 5 mL/min at atmospheric pressure. As shown in FIG. 12 for example, a counter-electrode 34 is fixed to a selectively movable translation stage 37 and is selectively disposed at a predetermined distance from the discharge end 24 of the capillary. This predetermined distance defines an electrode gap that is typically in the range of about 0.1 mm to about 5 mm.

As shown in FIG. 11 for example, an electric power source 40 is electrically connected via electrical leads 29a, 29b between the metallic section 25 of the capillary 22 and the counter-electrode 34 so that a potential difference can be placed between the counter-electrode and the metallic section of the capillary. As shown schematically in FIG. 1b for example, this power source 40 can be a direct current source. Alternatively, the power source 40 can be a radio frequency power source or a microwave frequency power source, as desired.

The LS-APGD device of the present invention is a glow discharge optical emission spectroscopy (GD-OES) source that operates at atmospheric pressure. One of the discharge electrodes of the LS-APGD device of the present invention is formed by the electrolytic solution, which may contain one or more analyte species. The passage of electrical current (either electrons or positive ions) across the solution/gas phase interface causes local heating and the volatilization of the analyte species. In contrast to the prior art ELCAD systems, the LS-APGD of the present invention totally consumes the aqueous electrolyte solutions at flow rates of up to about 2.0 mL/min, i.e., no water drips from the discharge end 24 of the capillary 22. At the flow rates in the range of about $1.0 \times 10^{-6}$ l/min to about 5 mL/min at atmospheric pressure of the LS-APGD of the present invention, the heat generated by the glow discharge 36 vaporizes the electrolyte solution that reaches the discharge end 24 of the capillary 22. As shown schematically in FIG. 14 for example, when an electrolyte solution 27 that has been electrified by the electrically conducting element of the capillary 22 is consumed as it emerges from the discharge end 24 of the electrified capillary, a glow discharge plasma 36 whose i-V characteristics are within the range of conventional, abnormal glow discharges operating in the 0.1 to 10 Torr pressure regime is created between the emerging surface of the exiting electrified electrolyte solution 27 and the counter-electrode 34.

As shown schematically in FIG. 11 for example, an injector 44 can be connected in fluid communication with the capillary 22 for introducing into the electrolyte solution flowing through the capillary, fluid that contains samples of materials to be analyzed. As shown in FIG. 11, a manual pump such as a syringe 45 can be provided and connected in fluid communication with injector 44 in order to provide a means for loading injector 44 with a reservoir supply of the desired sample.

Referring to FIG. 11 for example, the electrolyte solution is pumped from HPLC pump 30 and flows through the pump's output conduit 30a in the direction indicated by the arrow designated by the numeral 30b into injector 44. The electrolyte solution flows into and through injector 44 and exits via output conduit 44a in the direction indicated by the arrow designated by the numeral 44b into a liquid chromatography column 31 (described below) and from there into capillary 22. Manual rotation of the handle 43 of injector 44 determines whether the injector is configured and activated to introduce the predetermined sample into the stream of electrolyte solution that is flowing through the injector 44 and exiting the injector's output conduit 44a. An electrical lead 41 is attached to ground the portion of the output conduit 44a through which the electrolyte solution passes before the electrolyte solution enters liquid chromatography column 31.

Figure 1A:
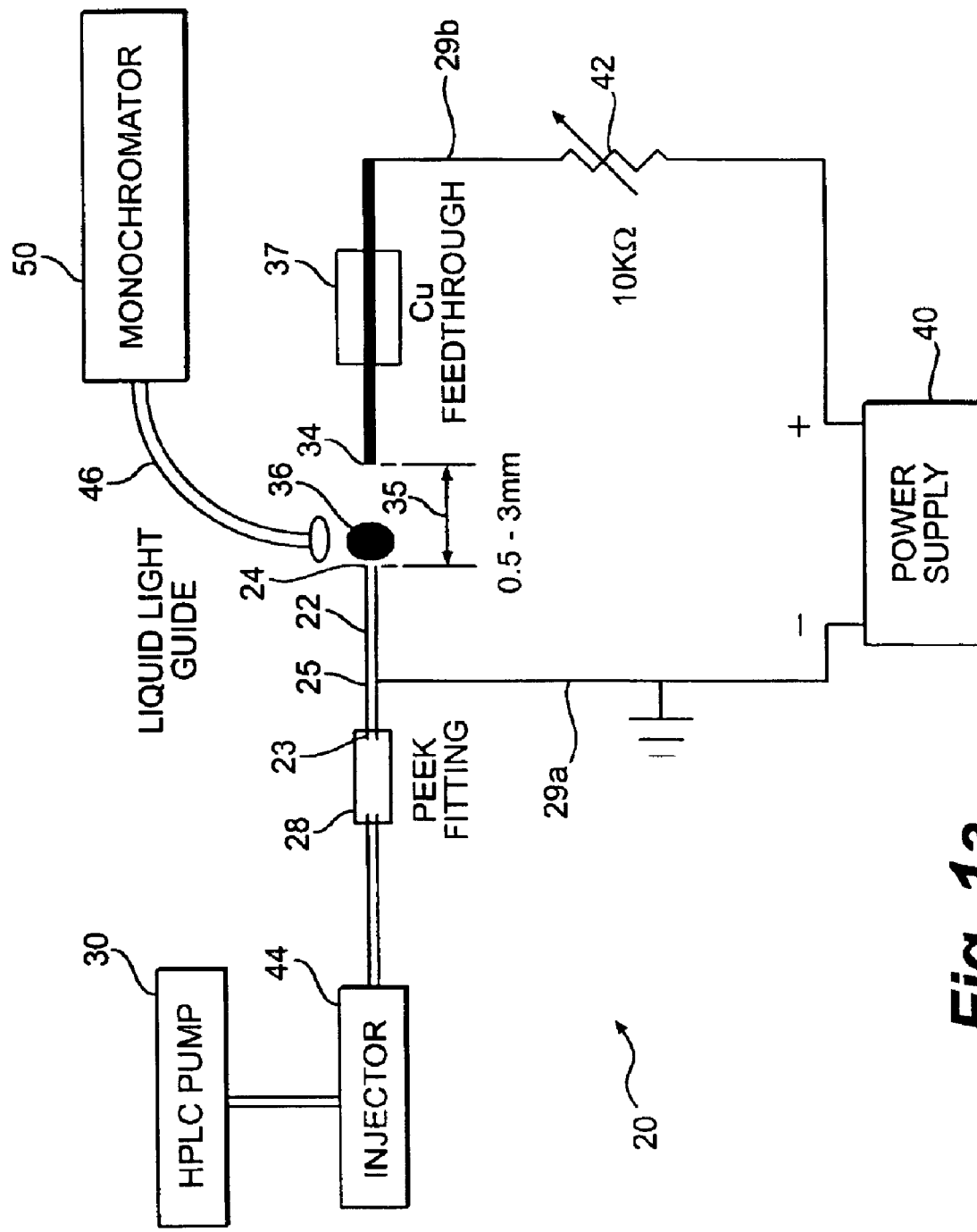
FIG. 1a is a diagrammatic representation of an embodiment of the liquid sampling-atmospheric pressure glow discharge (LS-APGD) apparatus of the present invention.

An alternative embodiment of the liquid sampling-atmospheric pressure glow discharge (LS-APGD) apparatus of the present invention is shown diagrammatically in FIG. 1a and is represented generally by the numeral 20. As shown in FIG. 1a for example, the source 20 includes a hollow capillary 22 having an inlet end 23 and a discharge end 24 opposite the inlet end. The capillary has an electrically conducting element in the form of a metallic section 25. In one suitable embodiment, the metallic section 25 of the capillary 22 desirably is formed of stainless steel, and the inside diameter of the capillary 22 can be 0.254 mm.

Figure 1B:
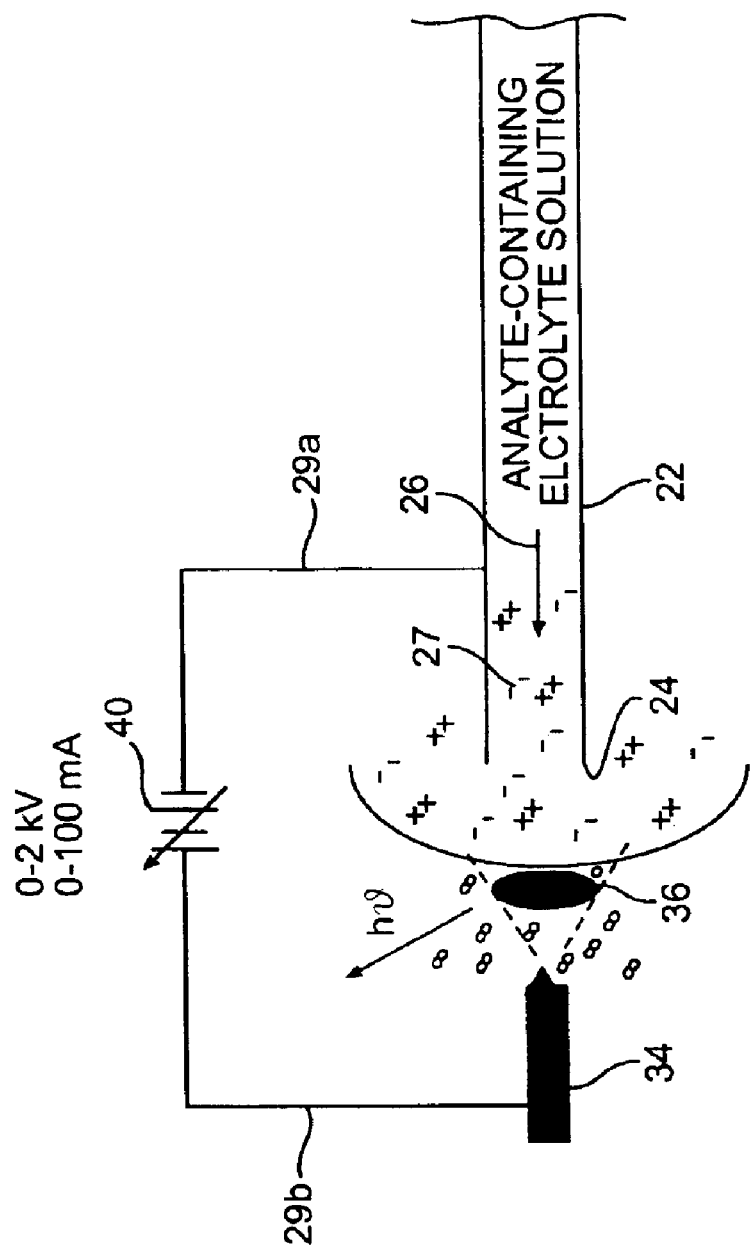
FIG. 1b is a diagrammatic representation of the operation of an embodiment of the liquid sampling-atmospheric pressure glow discharge (LS-APGD) apparatus of the present invention.

As shown schematically in FIG. 1b, the capillary 22 defines a longitudinal axis 26 aligned parallel to the direction of the flow of the electrolyte solution 27 through the capillary. In the embodiment shown schematically in FIG. 1b, the discharge end 24 of the capillary 22 is disposed such that the longitudinal axis 26 of the capillary at the discharge end 34 is disposed generally parallel to the horizontal direction defined as being perpendicular to the direction of the force of gravity. Moreover, as shown schematically in FIGS. 15A, 15B, 15C and 15D, the discharge end 24 of the capillary 22 is desirably disposed such that the longitudinal axis 26 of the capillary at the discharge end 34 is disposed generally parallel to the vertical direction defined by the action of the force of gravity. In this way, the electrolyte solution 27 that exits the discharge end 24 of the capillary 22 is flowing directly against the force of gravity. Thus, the force of gravity will not become an accelerating influence on the flow rate of the electrolyte solution 27 that exits the discharge end 24 of the capillary 22. Additionally, when the instrument is not in use, electrolyte solution 27 will not tend to drip out of the discharge end 24 of the capillary 22. However, orientations that are somewhere between the horizontal and vertical also are possible.

As shown schematically in FIGS. 1b and 14 for example, the discharge end 24 is a free end that desirably terminates in a plane that is perpendicular to the direction 26 of fluid flow upon exiting of the discharge end of the capillary. The discharge end 24 can be formed of material that is electrically conducting (such as metal for example), material that is electrically insulating (such as glass or fused silica for example) and/or material that is electrically semiconducting (such as silicon).

As schematically shown in FIGS. 1a and 1b for example, the counter-electrode 34 is axially aligned with the direction 26 of fluid flow upon exiting of the discharge end 24 of the capillary 22. In the presently preferred embodiments, the counter-electrode 34 is disposed vertically above the discharge end 24 of the capillary 22 such as shown schematically in FIGS. 15A, 15B, 15C and 15D with the arrow designated 26 indicating the direction of flow of the electrolyte solution in a vertical direction that is opposite to the direction of the gravitational force.

Figure 15A:
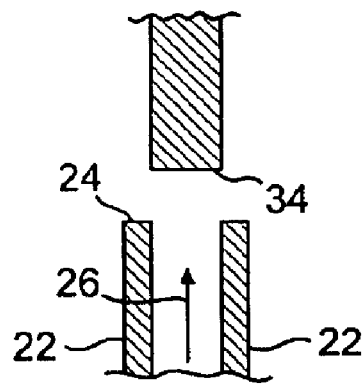
FIGS. 15A, 15B, 15C and 15D schematically present from a cross-sectional view, alternative relative orientations of the counter-electrode to the discharge end of the capillary.
Figure 15B:
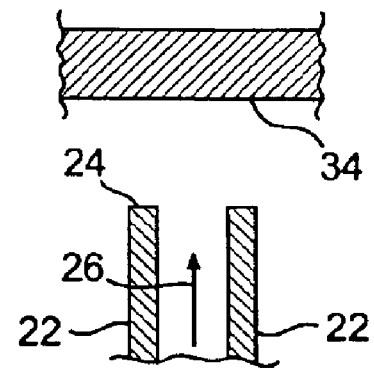
Figure 15C:
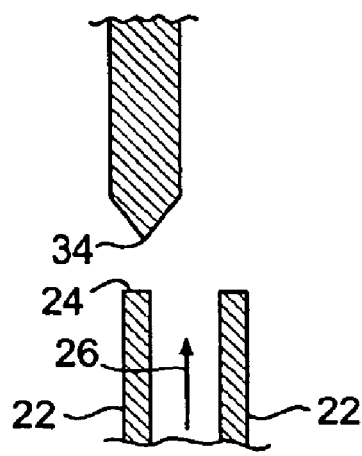
Figure 15D:
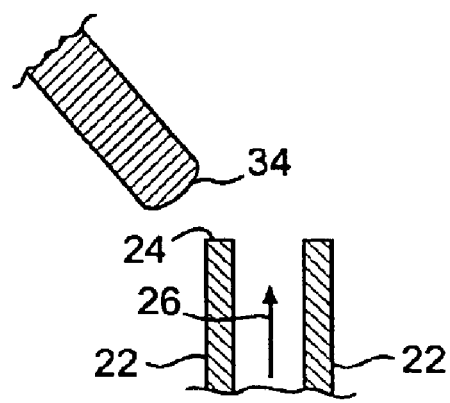

As shown schematically in cross-section in FIGS. 15A, 15B, 15C and 15D, the counter-electrode 34 can assume many different shapes and need not be disposed in symmetrical axial alignment with the axis 26 of the capillary 22. In FIG. 15A, the flat end of a rod forms the counter-electrode 34 that is disposed in symmetrical axial alignment with the axis 26 of the capillary 22 and thus the direction 26 of electrolyte flow from the discharge end 24 of the capillary 22. In FIG. 15B, a flat plate forms the counter-electrode 34. The counter-electrode 34 need not be disposed in symmetrical axial alignment with the axis 26 of the capillary 22. In FIG. 15C, the conical end of a rod forms the counter-electrode 34 that is disposed off-axis with the direction 26 of electrolyte flow from the discharge end 24 of the capillary 22. In FIG. 15D, the truncated spherical surface at the end of a rod forms the counter-electrode 34 that is disposed to one side and off-axis to the direction 26 of electrolyte flow from the discharge end 24 of the capillary 22.

Figure 13:
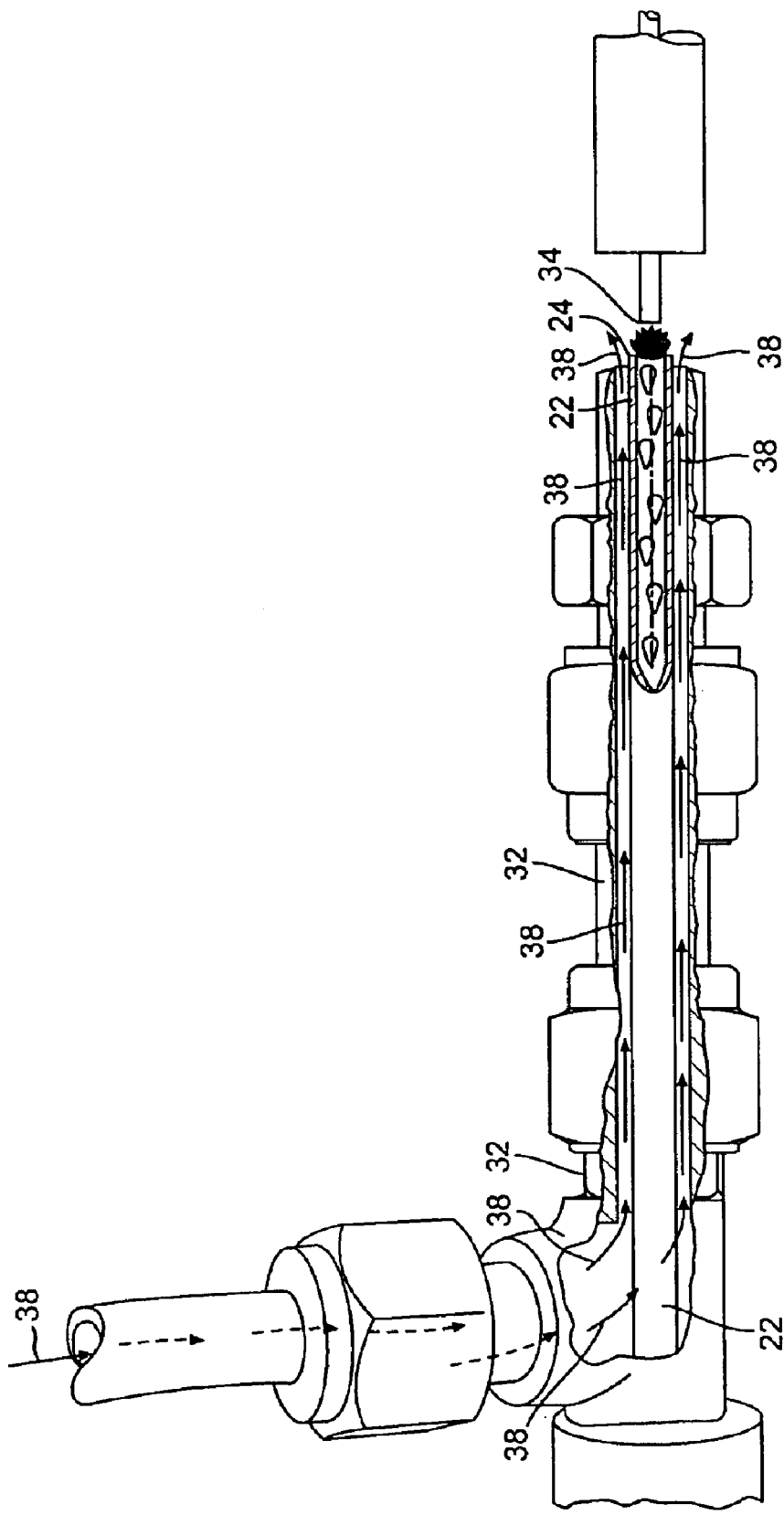
FIG. 13 is an expanded view with portions shown in cross section and portions shown cut away of a portion taken from FIG. 11.

In accordance with the present invention, a means can be provided for flowing gas around the discharge end of the capillary. The gas flowing means desirably can include a section disposed about the discharge end of the capillary. As shown in FIGS. 13 and 14 for example, the discharge end 24 of the capillary 22 can be surrounded by a conduit such as a concentric cylinder 32. This conduit 32 desirably can be connected to a supply of gas such as a canister 33 supplying nitrogen gas shown schematically in FIG. 11 for example. The flow of nitrogen gas (indicated schematically in FIGS. 13 and 14 by the arrows designated by the numeral 38) around the exterior of the discharge end 24 of the capillary 22 keeps the temperature of the discharge end 24 of the capillary from exceeding the melting temperature of the materials that form the discharge end 24 of the capillary 22. Additionally, as schematically shown in FIG. 14 for example, the gas 38 exiting from the annular space that is defined between the exterior of the discharge end 24 of the capillary 22 and the interior of the surrounding cylinder 32 is believed to tend to confine the plasma 36 more tightly around the longitudinal axis 26 of the discharge end 24 of the capillary 22. Furthermore, the gas 38 exiting from the annular space that is defined between the exterior of the discharge end 24 of the capillary 22 and the interior of the surrounding cylinder 32 is believed to create an environment that is especially conducive to the formation of the glow discharge 36 and helps improve the temporal stability of the plasma.

The electrically conducting element (e.g., metallic section 25) of the capillary 22 must be electrically insulated from the rest of the apparatus that is disposed upstream from the electrically conducting element. This can be accomplished for example by providing an electrically insulating conduit that forms the portion of the capillary 22 that is disposed upstream from the electrically conducting element (e.g., metallic section 25). Alternatively, the capillary 22 can be formed entirely of electrically insulating material and the electrically conducting element can be formed as an electrically conducting probe (such as a metal wire) that enters the interior of the capillary 22 through a side wall of the capillary. The inlet end 23 of the capillary can be formed of metal or of an electrically insulating material such as a polymer like poly-ether ether ketone (a.k.a. PEEK). As shown in FIGS. 1a and 12 for example, the electrically insulating portion of the capillary 22 can be connected to the metallic section 25 by using a fitting 28, which can be composed of metal or a polymer (a.k.a. a PEEK fitting).

A mechanism is provided for moving an electrolyte solution through the capillary and discharging the electrolyte solution out of the discharge end 24 of the capillary at a predetermined rate in the range of at least about $1.0 \times 10^{-6}$ l/min to about 2 mL/min at atmospheric pressure and more broadly in the range of at least about $1.0 \times 10^{-6}$ l/min to about 5 mL/min at atmospheric pressure. This can be accomplished in a number of ways. For example, as shown schematically in FIGS. 1a and 11, one such mechanism is a high precision liquid pumping system such as a high performance liquid chromatography (HPLC) pump 30. The inlet end 23 of the capillary 22 is connected in fluid communication with the outlet of pump 30. The HPLC pump 30 is configured so that the flow of electrolytic solution that is discharged out of the discharge end 24 of the capillary 22 occurs at rates in at least the range of about $1.0 \times 10^{-6}$ l/min to about 5 mL/min at atmospheric pressure. One example of such a suitable HPLC pump is a Waters (Milford, Mass.) Model 510 HPLC pump.

In an alternative example, the discharge of the electrolyte solution is accomplished by inducing electro-osmotic flow of the electrolyte solution through the capillary 22. As shown schematically in FIG. 1c for example, a direct current power supply 40 places an electric potential along the length of a section of the capillary 22 that terminates in the discharge end 24 of the capillary 22. Because of this potential, an electric field causes the positively charged particles in the electrolyte solution inside the capillary 22 to migrate toward the discharge end 24. As these positively charged particles move, they carry along the non-charged species due to the effect of the fluid's viscosity, and momentum carries the solution out of the discharge end 24 of the capillary 22. If the polarities on the counter-electrode and the electrically conducting element 25 are reversed, then the flowing charged species will have the reverse polarity.

In yet another alternative example, the flow of the electrolyte solution through the capillary 22 is accomplished by capillary action. In such an embodiment, the discharge of the electrolyte solution can be aided by the flow of the gas 38 exiting from the annular space between the exterior of the discharge end 24 of the capillary 22 and the interior of the surrounding cylinder 32. As schematically shown in FIG. 14 for example, this exiting gas flow 38 acts to draw out the electrolyte solution 27 from the discharge end 24 of the capillary.

As shown schematically in FIGS. 1a and 11–14 for example, a counter-electrode 34 is disposed at a predetermined distance from the discharge end 24 of the capillary 22. As shown schematically in FIG. 1b, the discharge end 24 of the capillary 22 and the counter-electrode 34 form the input and output electrodes of the LS-APGD apparatus 20. As shown schematically in FIG. 1a by the line designated by the numeral 35, the predetermined distance between the discharge end 24 of the capillary 22 and the counter-electrode 34 defines an electrode gap 35 in which the plasma 36 (glow discharge) is formed. A 2.4 mm diameter solid copper rod provides a suitable counter-electrode 34. As shown schematically in FIGS. 1a, 11 and 12 for example, one or both of the input and output electrodes can be mounted on a translation stage 37 that is selectively movable so that the gap 35 (FIG. 1a) between the electrodes can be varied.

While counter-electrode is shown aligned (at 180 degrees) with the longitudinal axis 26 of the discharge end 24 of the capillary in FIG. 1b for example, in any desired configuration where additional room is needed close to the glow discharge 36, the counter-electrode 34 can be aligned parallel but off-axis or asymmetrically intersecting the axis 26 but to the side. One such desired non-axial configuration would be to accommodate the inlet of a mass spectrometer.

As shown schematically in FIGS. 1a and 11 for example, a power source 40 is connected between the capillary 22 and the counter-electrode 34 so as to place a potential difference in the range of about 200 to 1,000 volts between the discharge end 24 of the capillary 22 and the counterelectrode 34. As shown schematically in FIG. 1b, the output of the power source 40 can be varied by the operator. Moreover, the power source can be a radio frequency power source or a microwave frequency power source or a direct current power source, as desired. A suitable direct current power source for maintaining the atmospheric pressure glow discharge (APGD) can be provided by a Kepco (Flushing, N.Y.) Model BHA 2000-0.1M power supply that is electrically connected to the input and output electrodes. In an alternative embodiment that is schematically shown in FIG. 1c for example, the same power supply 40 that is used to create the electro-osmotic effect needed to move the electrolyte solution through the capillary 22, can be used to provide the power needed to maintain the plasma 36 that produces the glow discharge 36 at atmospheric pressure.

The electrically insulating conduit that can be provided to form the inlet end 23 of the capillary 22 electrically isolates the high voltage that is applied to the metallic section 25 of the capillary 22. It also may be desirable to add ballast to the discharge circuit that is formed by the metal section 25 of the capillary 22, the power source 40, the counter-electrode 34, and the plasma 36 from which the glow discharge emanates. Accordingly, as schematically shown in FIG. 1a, the high voltage that the power source 40 applies to the powered electrode is desirably coupled through a variable resistor 42 such as a 10 k$\Omega$ variable resistor. Similarly, in the alternative embodiment that is schematically shown in FIG. 1c for example, a secondary electrical power source 39 can be used to ensure that an electrical potential difference exists between the discharge end 24 and the counter-electrode 34 in order to maintain the glow discharge 36.

Figure 1C:
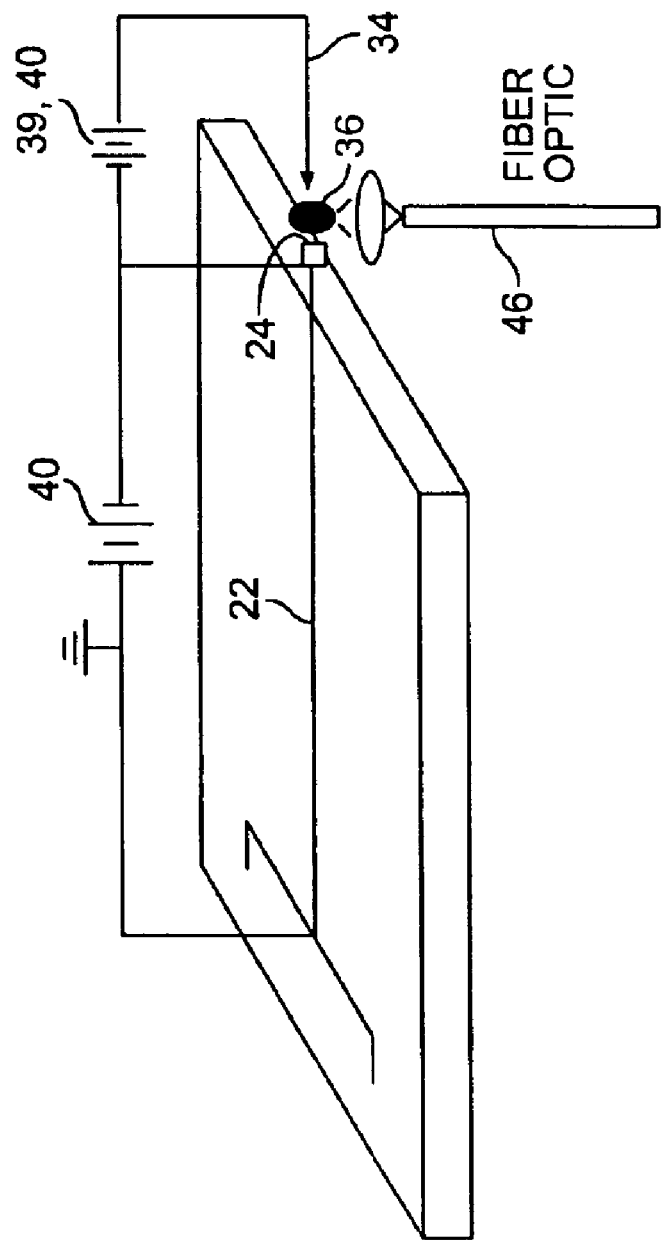
FIG. 1c is a diagrammatic representation of an embodiment of the liquid sampling-atmospheric pressure glow discharge (LS-APGD) apparatus of the present invention configured as an integrated detector for lab-on-a-chip applications.

As schematically shown in FIGS. 1a, 1b and 1c, the counter-electrode 34 typically is the powered (or input) electrode, and the capillary 22 is typically the output electrode. However, very different from the cited ELCAD sources, the apparatus of the present invention affords the operator the option of applying discharge voltages in each of four ways: (1) the electrolytic solution grounded as the anode of the circuit; (2) the electrolytic solution powered as the anode of the circuit; (3) the electrolytic solution grounded as the cathode of the circuit; and (4) the electrolytic solution powered as the cathode of the circuit. The electrode that is at the more negative potential always serves as the cathode. Thus, the electrically conducting element (such as metallic section 25) of the capillary 22 can be electrically connected to the electrical power supply 40 so as to become the powered (or input) electrode while the solid copper rod 34 can become the output electrode.

Using a convention that is consistent with the previous ELCAD works, the situation wherein the electrolyte is grounded via grounding of the electrically conducting element such as metallic section 25 of the capillary 22 (as shown in FIG. 1a for example) and a positive voltage is applied to the copper counter electrode 34, is termed the "normal" polarity mode and is shown in FIGS. 11, 1a, 1b and 1c for example. Similarly, the opposite configuration, i.e., where the electrolyte is attached to the positive output of the power supply via attachment of the electrically conducting element (such as metallic section 25) of the capillary 22 and the copper rod 34 is grounded, is termed the "reversed" polarity mode.

As schematically shown in FIGS. 11 and 1a, a fluid injector 44 can be connected in fluid communication with the capillary 22. The injector 44 is desirably configured for introducing into the capillary 22, fluid containing analyte, i.e., samples of materials to be analyzed. A Rheodyne (Cotai, Calif.) Model 7725i sample injector valve provides one example of a suitable injector 44 and functions to permit the introduction of a precise and discrete volume of the sample into the flowing electrolyte solution.

Moreover, in some cases it may be desirable to separate the analytes in the electrolyte solution before they are discharged from the free end of the capillary and introduced into the plasma that forms in the gap between the electrodes. One way to accomplish this is by passing the electrolyte solution through a mechanism such as a chromatography column. The chromatography column can be configured to effect the separation by one of the following techniques: normal phase liquid chromatography, reverse phase liquid chromatography, ion chromatography, and capillary electrochromatography. Capillary zone electrophoresis could also be employed to effect such a separation. In anticipated commercial environments, it is desirable to perform the chromatographic separation prior to introduction into the flowing electrolyte stream. For example, the chromatographic separation would be performed on the native sample taken from an environment such as a polluted stream before the sample was introduced in its separated form into the flowing electrolytic solution.

As schematically shown in FIG. 11 for example, a liquid chromatography column 31 can be included to define a section of the fluid pathway through which the electrolyte solution flows toward the discharge end of the capillary 22. The chromatography column 31 desirably is disposed downstream of the injector 44 and upstream of the electrically conducting element (such as metallic section 25) of the capillary 22. In this way, the species in the electrolyte solution and in the injected sample of analyte are segregated before being discharged out of the discharge end 24 of the capillary 22 and introduced into the plasma 36 that is maintained in the gap between the counter-electrode 34 and the discharge end 24 of the capillary 22.

Figure 16:
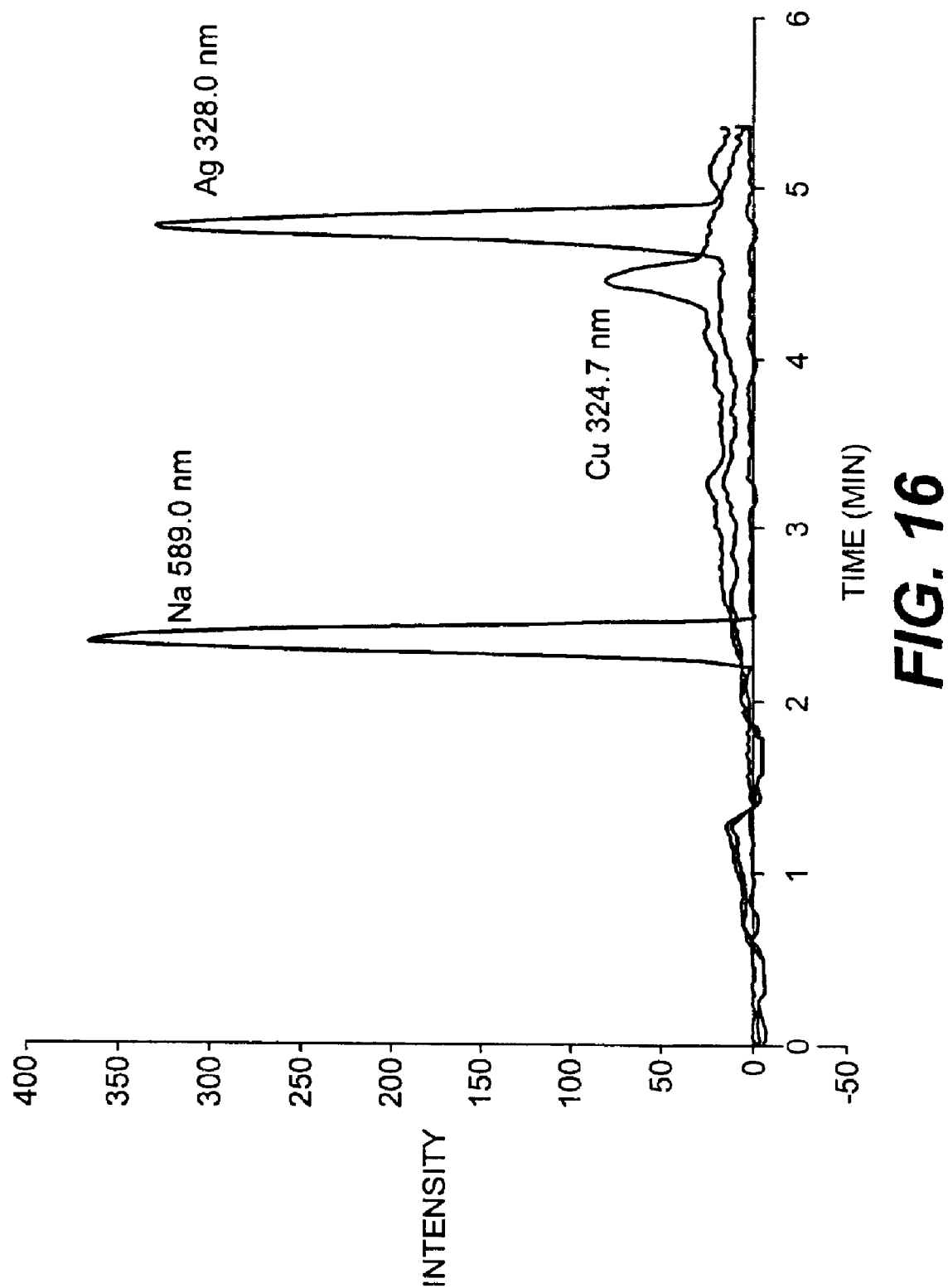
FIG. 16 is a graphic representation of an optical emission chromatogram for the isocratic elution of 5.0 mM HCl in Milli-Q water. Separation of 300 ppm Ag and Cu, 100 ppm Na using a Universal Cation column and an embodiment of the LS-APGD of the present invention. Flow rate=300 µL/min, discharge current=40 mA, electrode gap=0.5 mm.

The result of the use of the LS-APGD apparatus in performing a separation of 300 ppm Ag and Cu, 100 ppm Na using a Universal Cation column is shown for example in FIG. 16, which is a graphic representation of an optical emission chromatogram for the Isocratic elution of 5.0 mM HCl in Milli-Q water. Flow rate=300 $\mu$L/min, discharge current=40 mA, electrode gap=0.5 mm. In simple terms, as shown in FIG. 11 for example, the liquid chromatograph (HPLC) column 31 is used to separate the three cationic species so that they can be quantified individually as they exit the column 31 and flow into the plasma 36 that forms at the discharge end 24 of capillary 22. The LS-APGD of the present invention provides a simpler and less expensive means of performing the detection portion of the analysis than current methods like HPLC coupled to inductively coupled plasma optical emission or to mass spectrometry.

One or more instruments can be used to analyze the constituents of the electrolyte solution, with or without any additional analytes that might be injected into the electrolyte solution flowing through the capillary 22. As schematically shown in FIGS. 11, 12, 1a and 1c for example, a light directing element 46 is desirably disposed to direct to a suitable analyzing instrument, the electromagnetic radiation from the glow discharge 36 that forms in the electrode gap. A suitable light directing element 46 can include a fiber optic light guide. As shown schematically in FIG. 1a for example, one end of a 3 mm core diameter liquid light guide 46 (available from Edmund Industrial Optics, Barington, N.J.) can be disposed so as to sample optical emission from the plasma 36 formed in the electrode gap 35.

The opposite end of the light guide 46 can be coupled to an instrument 50 for analyzing electromagnetic radiation that emanates from the glow discharge. A suitable such analyzing instrument 50 can include a monochromator. As shown schematically in FIG. 1a for example, the opposite end of the light guide 46 can be coupled to the entrance slit of an optical spectrometer 50 such as a Digikrom Model 240 monochromator (CVI Laser Corp., Albuquerque, N. Mex.) 0.24 m Czerny-Turner spectrometer equipped with a 2400 groove/mm holographic grating for optical analysis and monitoring of the emission from the sample. The control interface of the monochromator can be used to adjust the scanning range, slit width, spectral calibration, and wavelength selection of the monochromator.

A photo-multiplier tube (e.g., from Hamamatsu, Bridgewater, N.J. Model) can be disposed to detect the optical emission signals. An analog current meter can be connected to the photo-multiplier tube and can convert the optical emission signals into voltage signals. A Macintosh IIsi computer can be employed to record the output of the current meter via a National Instruments (Austin, Tex.) NB-MIO-16X interface board. An X-Y recorder-type program within the National Instruments LabView 2 software environment can be used to record the data. The obtained digital data can be processed and managed in the form of Microsoft (Seattle, Wash.) Excel files.

A mass spectrometer is another instrument that can be used to analyze the constituents of the electrolyte solution, with or without any additional analytes that might be injected into the electrolyte solution flowing through the capillary 22. A commercial inductively coupled plasma mass spectrometer such as a Model ELAN 6100 instrument available from Perkin-Elmer/Sciex, Ontario, Canada, can be disposed near the plasma 36 in a conventional manner for analyzing ions that emanate from the glow discharge. In one possible implementation, analyte species that are ionized through collision with electrons, excited state, or ionic species are sampled via the ion optics that extracts ionic species from the plasma 36 and directs them to a quadrupole mass analyzer for example. The masses of the molecules and atoms constituting the liquid flow are analyzed by a mass spectrometer such as a quadrupole mass filter (or another type of mass analyzer) that is configured to allow ions with a given mass/charge ratio to reach a detector. As is conventional, a turbo molecular pump can be employed to maintain the mass spectrometer under reduced pressure.

EXAMPLES

Each of the test solutions was prepared with HPLC-grade water (Fisher Scientific, Pittsburgh, Pa.) adjusted to the appropriate pH with concentrated nitric acid (Fisher Scientific, Pittsburgh, Pa.) or pLi with lithium carbonate (Alfa Aesar, Ward Hill, Mass.). Analyte standard solutions were prepared from Specpure (Alfa Aesar, Ward Hill, Mass.) AAS standards (1000 Fg/mL in 5% $HNO_3$).

Figure 2A:
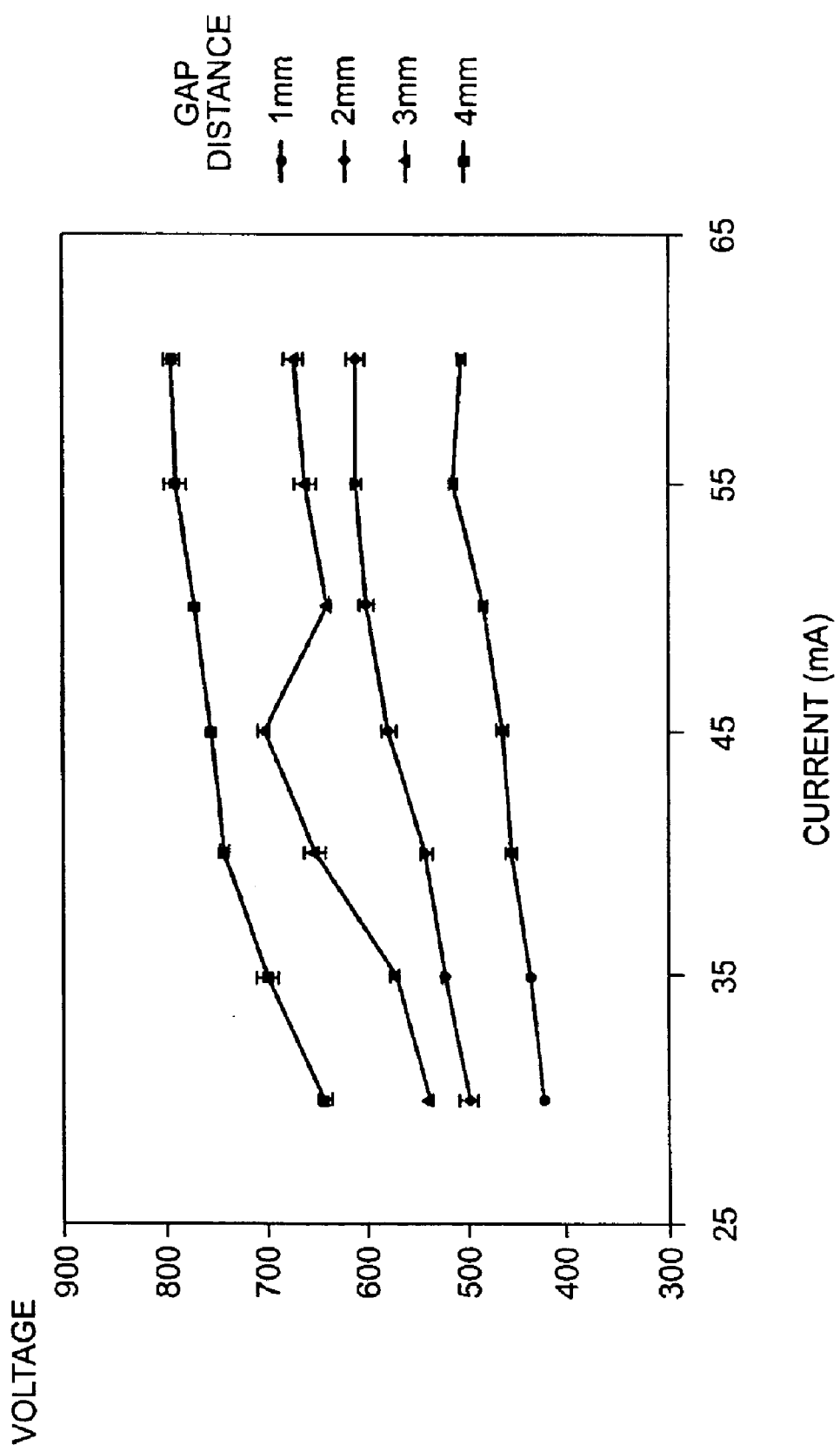
FIG. 2a is a graphic representation of the current-voltage characteristics of an embodiment of the LS-APGD for different inter-electrode gap distances at normal polarity. Solution flow rate=1.5 mL/min., $HNO_3$:HPLC water electrolyte, pH=1.

Discharge operation parameters—All direct current-powered glow discharge sources, whether operating in reduced pressure or atmospheric pressure, operate in fairly well defined regimes of current and voltage and i-V relationships. The previous ELCAD works clearly exhibit classical abnormal GD plasma behavior. In addition to the current, the discharge voltage was seen to be dependent on the inter-electrode gap and the pH of the solution (aqueous nitric acid). As seen in FIG. 2a for example, the i-V curves for the LS-APGD device are more or less typical of GD sources. As might be expected, the required discharge voltage increases with the inter-electrode gap.

Somewhat surprising, the slopes of the respective curves are quite shallow, with the apparent resistances (3–4.5 Ω) being very similar across the families. This behavior detected in data obtained using the apparatus and method of the present invention indicates that the models that have been proposed in prior art discussions for the ELCAD plasmas, wherein sputtering by water molecules releases cations, may not be correct. If sputtering by water molecules releases cations, then the reversed polarity plasmas would not be operational, at least with such similar i-V characteristics. The data obtained using the apparatus and method of the present invention suggest that the operation mechanism is more akin to a discharge composed of both water and air originating species as the conductive elements (ions) in the plasma.

It is very important to mention that in both powering schemes using the apparatus and method of the present invention, the aqueous solutions are totally consumed at these flow rates, i.e., no water drips from the discharge end 24 of the capillary 22. This is another difference with the ELCAD devices where high flow rates (1–10 m/min) produce a waterfall flow into the collection reservoir. At low discharge currents, it is clearly seen that a fine aerosol is generated, most likely through resistive heating of the surface of the solution. Varying the flow rate between 1 to 5 mL/min resulted in little or no change in operating voltage at any current, although an increased flow rate did allow the glow discharge to form while using increased inter-electrode gap distances.

It is very interesting to note that in using the apparatus and method of the present invention the operating voltages for the case of the reversed polarity arrangement are lower than for the normal case. In the low current regimes, the difference is approximately 10% lower. While at the higher end of the range the differences grow to 20–25% (as the differences in slope suggest). On a first principles basis, given the fact that the gas phase composition of both plasmas is the same, the reason for the higher discharge voltage in the case where the electrolyte solution is the cathode, must lie in the differences in the secondary electron yields of water versus the copper counterelectrode. The majority of electrons responsible for ionization in the gas phase are generated by ion bombardment of the cathode. So the energy cost of this process is a key factor, much as it is in the conventional low-pressure glow discharge sources, in determining the discharge voltage that is needed for sustaining the glow discharge. In low pressure GD sputtering systems, the maintenance potential is related to the electron binding energy in the solid. While there is no analogy for liquid water, the fact that $H_2O$ has a higher ionization potential than most metals would suggest that the binding energy for electrons to bulk water would require greater energy as well.

Figure 3A:
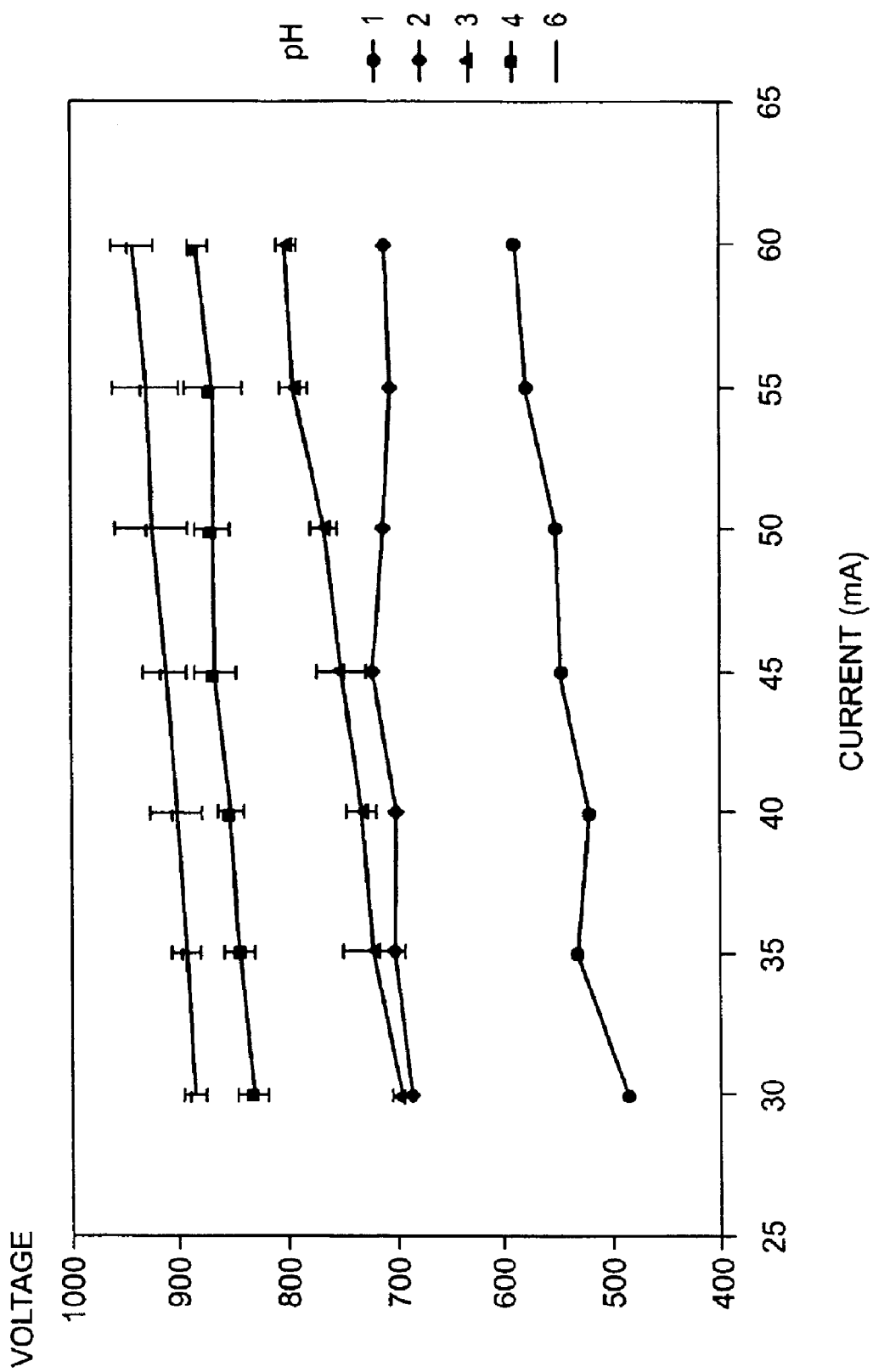
FIG. 3a is a graphic representation of the effect of electrolyte solution pH on the current-voltage characteristics of an embodiment of the LS-APGD at normal polarity. Solution flow rate=1.5 mL/min. inter-electrode gap=1 mm.

If the proposed explanation of the i-V responses is correct, then factors that affect the resistivity of the electrolyte solution should have fairly straightforward effects on the operating voltages. As shown in the previous ELCAD studies, pH is such a factor. FIG. 3a depicts the i-V curves obtained as a function of the solution pH, as dictated by the concentration of the nitric acid electrolyte at a fixed flow rate of 1.5 mL/min and an inter-electrode gap of 1 mm. Clearly seen is a large dependence on pH, wherein the solutions with highest proton content (i.e., low pH) require much lower operating voltages than those approaching neutral conditions.

Figure 3B:
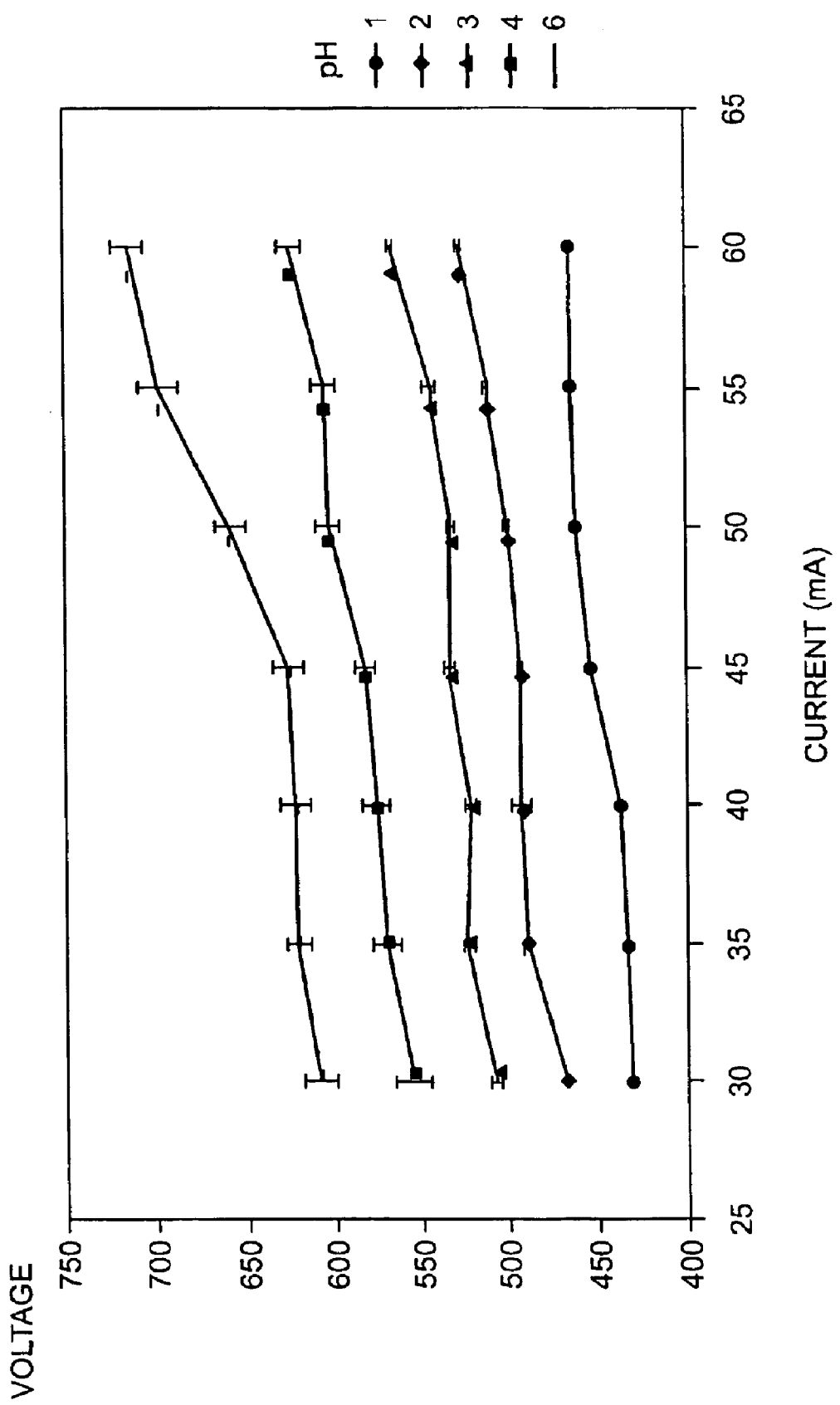
FIG. 3b is a graphic representation of the effect of electrolyte solution pH on the current-voltage characteristics of an embodiment of the LS-APGD at reversed polarity. Solution flow rate=1.5 mL/min. inter-electrode gap=1 mm.

Very interestingly, the slopes of the responses (i.e., resistance) depicted in FIG. 3a do not depend heavily on the pH. This seems to reinforce the suggestion that the slopes of the response curves are dictated by the gas-phase plasma resistance and not the solution conductivity. In fact, the differences here suggest that electrolyte concentration affects the breakdown voltages in much the same way as the inter-electrode gap. It is also easy to see that the plasmas ignited at low pH values operate much more stably than those of low conductivity. The same general response is seen in FIG. 3b for the case of the reversed polarity experiments. Low pH values yield low discharge voltages, while higher pH values require greater voltages and operate in a less stable manner.

Figure 4A:
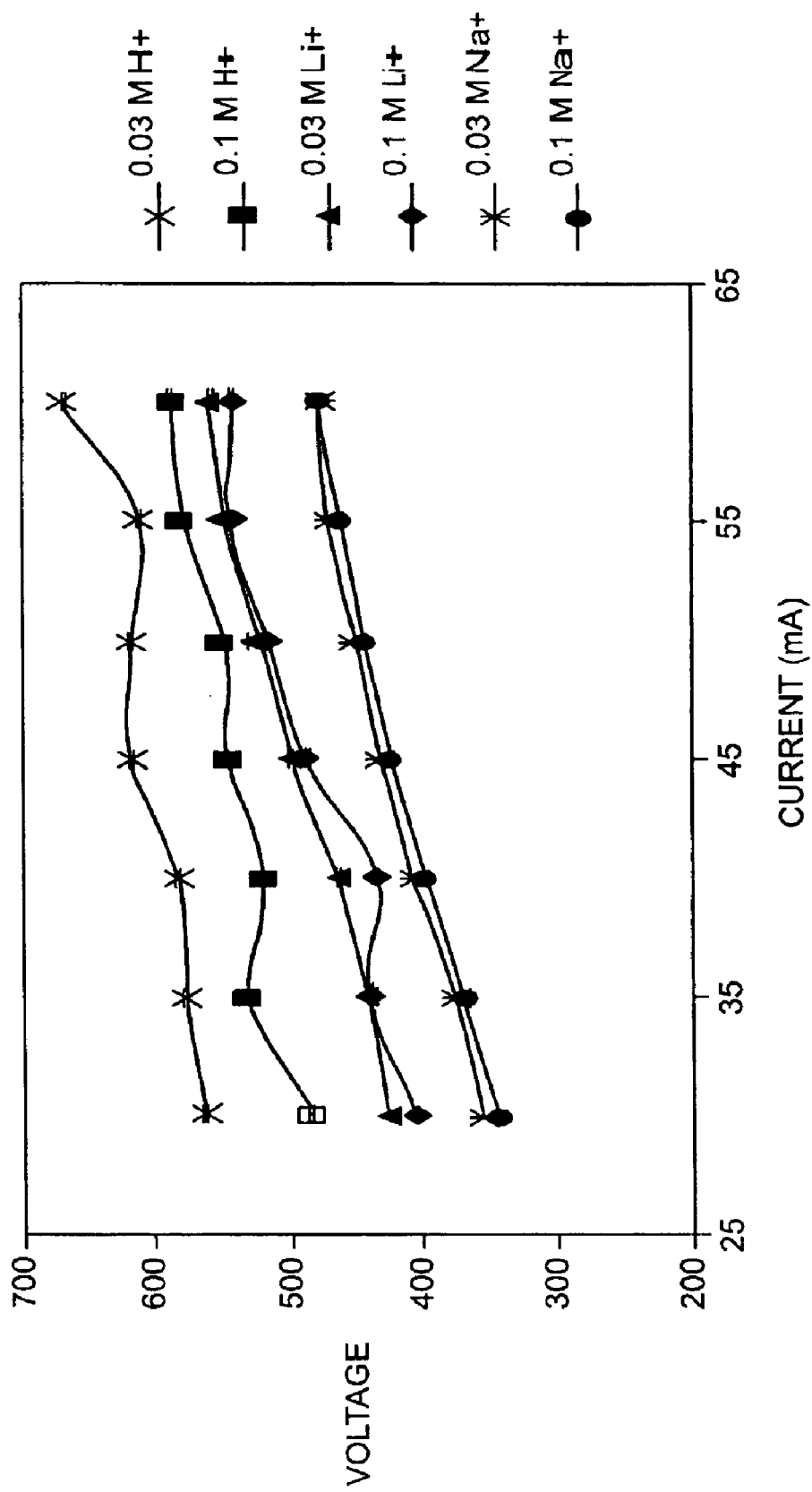
FIG. 4a is a graphic representation of the effect of Na+, Li+ and H+ concentrations on the i-V characteristics of an embodiment of the LS-APGD device at normal polarity. Solution flow rate=1.5 mL/min. inter-electrode gap=1 mm.

Since there is a definite role of pH in the operating voltage of the LS-APGD device of the present invention, it is natural to question whether the effect of the pH is related specifically to the identity of the hydronium ion ($H_3O^+$) that becomes the mobile electrolyte in the solution. Alternatively stated, is the most important factor the simple existence of a hydrated cation to effect a conductive path between the solution and the electrode. As shown in FIG. 4a, the operating voltage of the plasma is in fact lower for the case where either $Li^+$ or $Na^+$ is the cation. For both the case of 0.1 and 0.03M electrolyte concentrations, the maintenance voltage for the Li-containing solution is approximately 50 volts lower than the hydronium ion case and about 100 volts lower for the Na-containing solutions. Note the fact that the slopes of the i-V curves depicted in FIG. 4a are fairly independent of the electrolyte identity and concentration. Accordingly, the apparatus of the present invention also differs from the cited ELCAD sources, in affording the operator of the present invention the ability to move electrolyte solution having primary species other than just the $H^+$ (hydronium) species. This fact further reinforces the conclusion that the plasma resistance is related to the gas phase processes rather than to the composition of the solution.

Figure 4B:
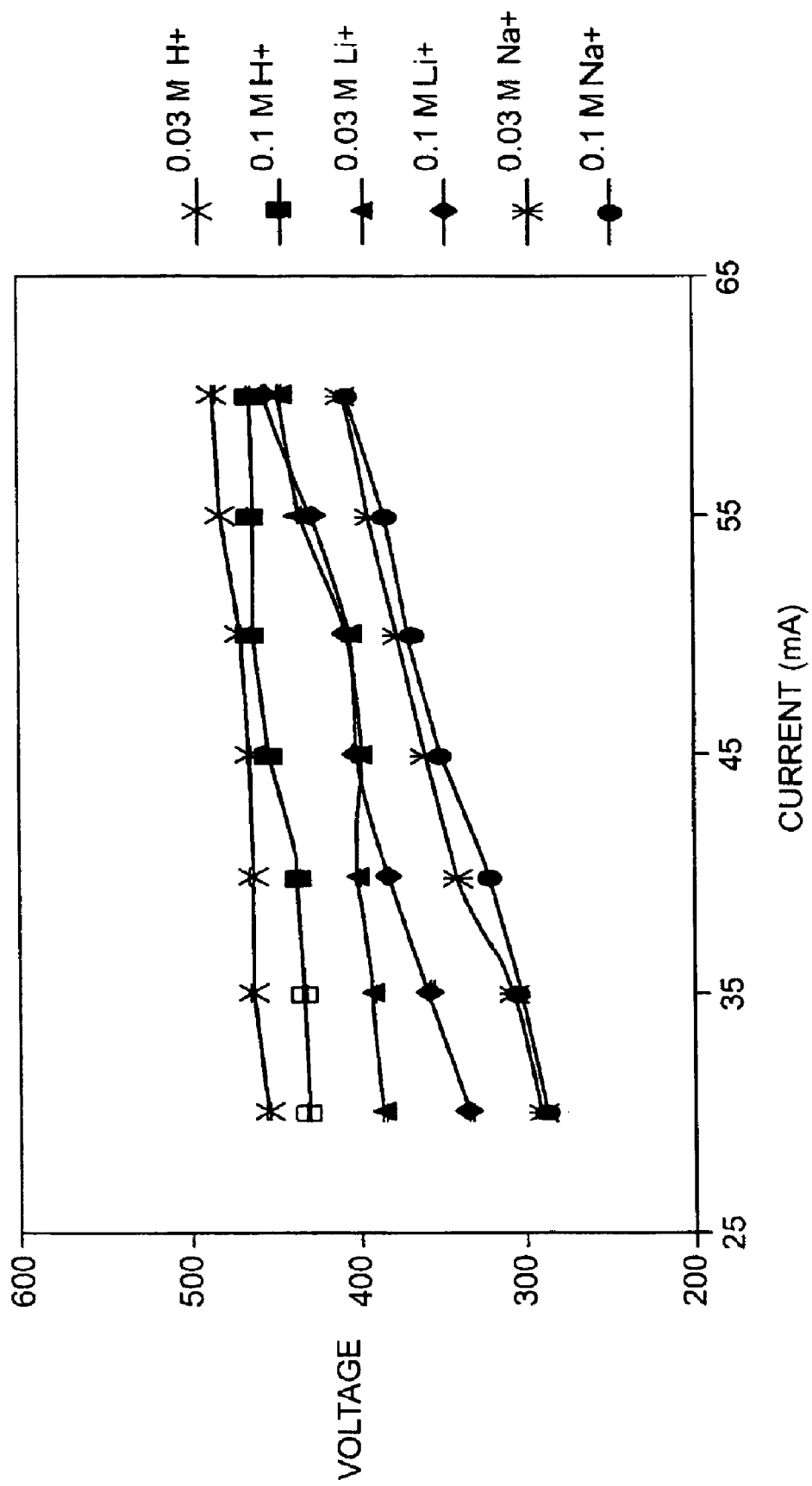
FIG. 4b is a graphic representation of the effect of Na+, Li+ and H+ concentrations on the i-V characteristics of an embodiment of the LS-APGD device at reversed polarity. Solution flow rate=1.5 mL/min. inter-electrode gap=1 mm.

As shown in FIG. 4b, similar to the results obtained in the experiments of others noted above, the operating voltages are lower in the case of the reversed polarity operation mode. The plasma resistance also appears to be lower than for the normal polarity mode. The fact that the plasma source operates at lower voltages with the $Li^+$ and $Na^+$ electrolytes suggests that the "ionization potential" of the electrolyte, or more correctly that of the solvated cation, dictates the potential that is necessary in order to produce the plasma. As suggested previously, it is the ability to release charged species from the solution surface that is fundamental to the operation of the plasma and indeed to the breakdown voltage.

On a simplified level, the establishment of the glow discharge at the surface of a liquid seems to be analogous to the breakdown that occurs at the surface of a solution in the case of electrospray ionization sources. Interestingly, the trend in operation voltage for the $Li^+$ and $Na^+$-electrolyte solutions corresponds to the free energy of formation of hydrated ($-\Delta G_{sol}^\circ$) and isolated ($-\Delta G_{o,m}^\circ$) Li and Na ions found from electrospray sources. Therefore, since the formation of gaseous, hydrated Na ions is more energetically favorable, one might expect that the voltage required in order to produce the same process in the LS-ASGD would be lower as well. The free energy of formation ($-\Delta G$) values are found to be inversely related to the diameter of the solvated cation species. Tang and Kebarle do not provide corresponding thermodynamic data for hydronium ion in solution. Therefore, the smaller hydronium ion would indeed be expected to require a higher discharge voltage.

Figure 5:
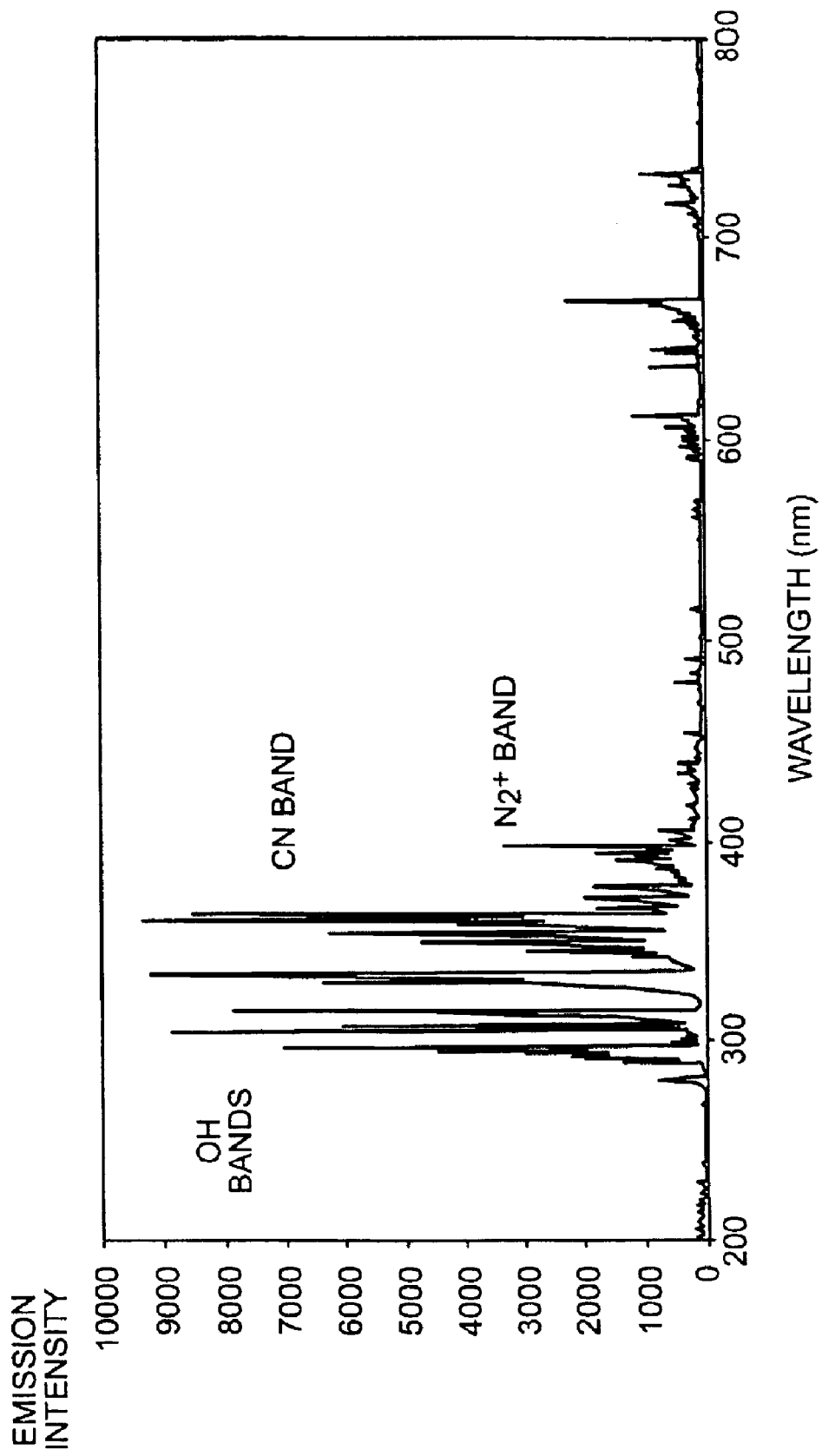
FIG. 5 is a graphic representation of the optical emission spectrum from the introduction of pH 1 deionized water electrolyte solution in an embodiment of the LS-APGD of the present invention. Solution flow rate=1 mL/min, discharge current=40 mA, inter-electrode gap=1 mm.

LS-APGD Optical Emission Spectra—Based on the fact that the electrolyte solution that contains the analyte is totally consumed when employing the LS-APGD apparatus and method of the present invention, one must assume that the composition of the plasma in the region just above the surface of the electrolyte solution is composed of a high percentage of both water and atmospheric gases. These two components will then be expected to dominate the resultant optical emission spectra. As shown in FIG. 5, this is indeed the case. The spectrum of a pH=1 de-ionized water solution is dominated by band structure of $OH^-$, $N_2$, and $N_2^+$, and is (not surprisingly) comparable to that obtained from combustion flames operating at atmospheric pressure. Different from "conventional" GD emission sources, spectral band interferences will be an important consideration in the choice of analyte transitions.

Figure 6:
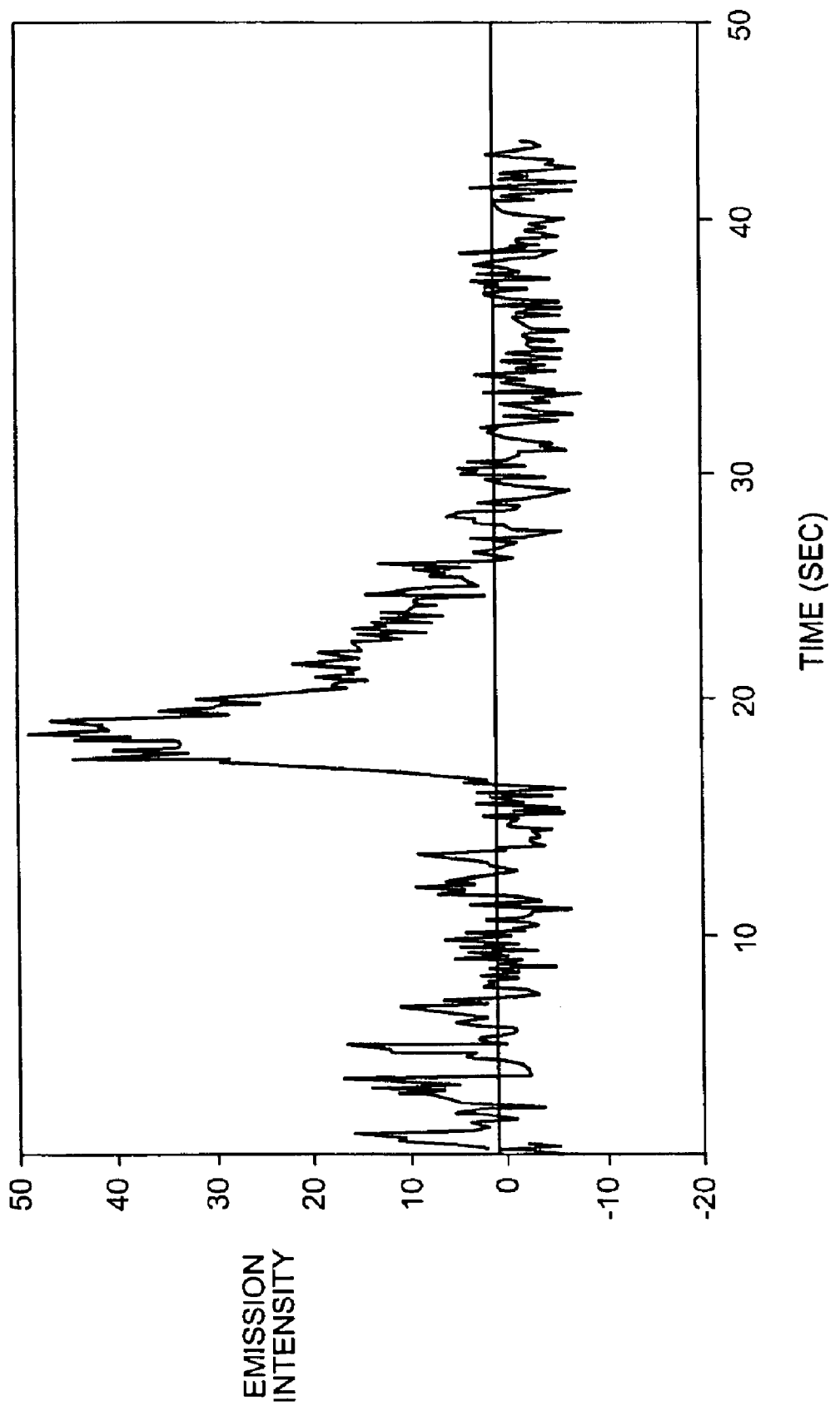
FIG. 6 is a graphic representation of Na (I) 589.0 nm optical emission transient for the introduction of a 5 µL aliquot of a 50 ppm nA solution in an embodiment of the LS-APGD of the present invention. Electrolyte pH=1, flow rate=1 mL/min, discharge current=40 mA, electrode gap=1 mm.

Different from the previous ELCAD systems, the LS-APGD of the present invention is well suited for the introduction of discrete samples either in a flow injection mode or in a chromatographic mode. FIG. 6 depicts a typical emission response transient for the embodiment of the present invention that is schematically depicted in FIG. 1a, specifically for a 5 μL injection of a 60 ppm Na solution (as 5% $HNO_3$) introduced in a pH 1 solution flowing at a rate of 1 mL/min. The transient exhibits a fairly steep leading edge as the analyte plug enters the plasma region, though there is some signal spread over a time period of approximately 10 seconds. The initial portion of the peak (on the order of 3 seconds) is believed to be a reflection of the band broadening of the analyte-containing solution, with the latter tailing being due to condensation and subsequent volatilization of analyte from the solid counter-electrode.

In the remainder of the described studies, all of the optical emission data are collected from the plasma operated in the mode wherein the electrolyte solution serves as the cathode. The reversed geometry, while able to operate quite stably, does not produce as intense photon fluxes from the aqueous analyte as the normal geometry produces. At present, this appears to be related more to the fact that the negative glow (i.e., excitation region) of the plasma settles near the surface of the cathode, rather than any appreciable differences in volatilizing the analyte-containing solution. Simply, transport of analyte vapor into the negative glow is more efficient when the electrolyte solution acts as the cathode.

Analyte Emission Response as a Function of Discharge Conditions and Electrolyte Composition—In conventional low-pressure GD sources, the role of discharge current is essentially two-fold, though not explicitly a first order relationship. First, as discharge current is increased, sample ablation rates increase to provide greater numbers of analyte atoms to the negative glow region. Second, increases in current result in greater numbers of electrons within the negative glow, and these electrons are available to excite the sputtered atoms.

Figure 7:
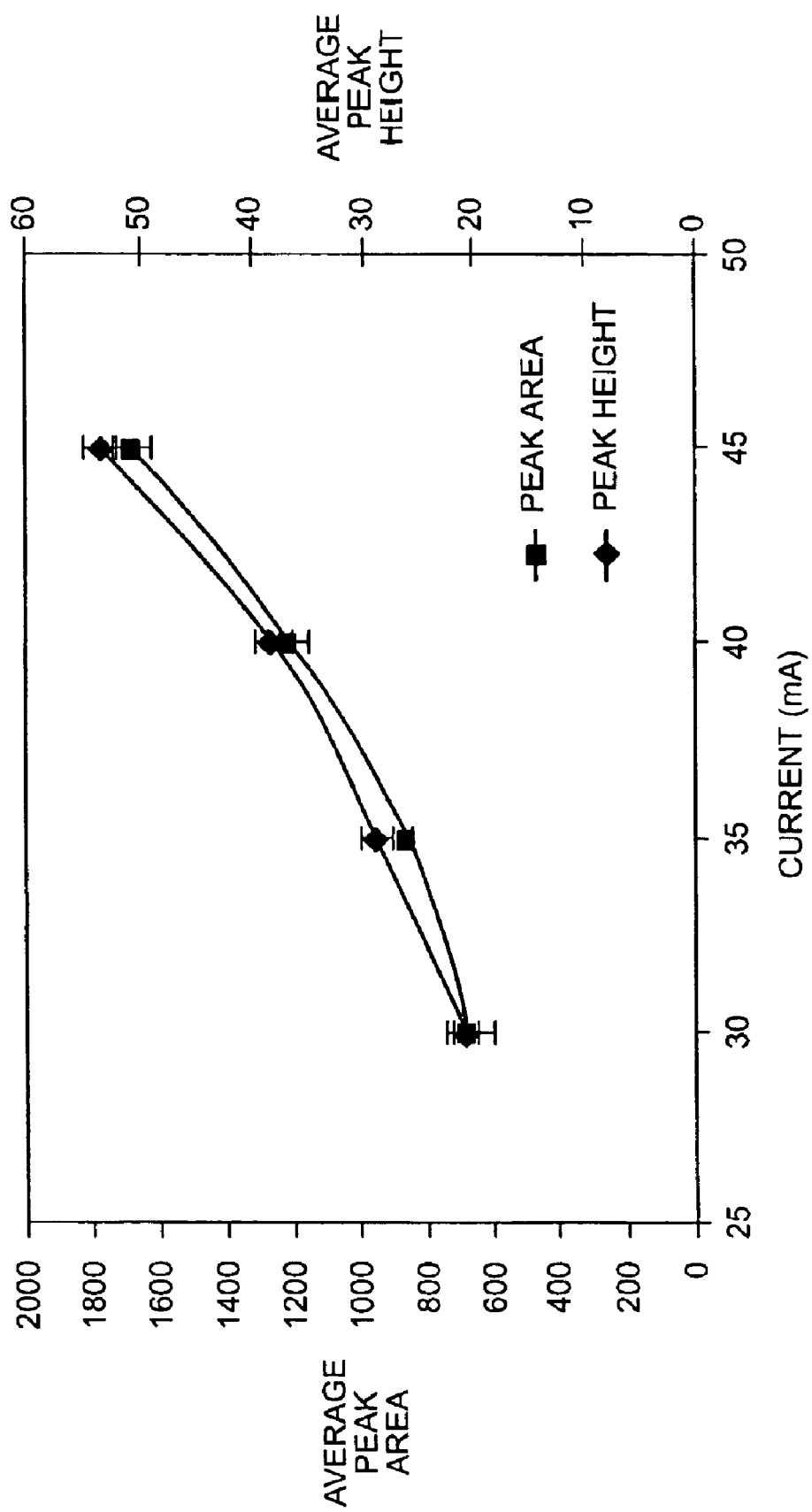
FIG. 7 is a graphic representation of the effect of discharge current on the response of Na (I) 589.0 nm transient peak height and area in an embodiment of the LS-APGD of the present invention. Triplicate injections of 5 µL aliquot of a 50 ppm Na solution. Electrolyte pH=1, flow rate=1 mL/min, discharge current=40 mA.

As shown in FIG. 7, the emission response for introduced Na analyte is related to the discharge current, both in terms of transient peak height and area. Interestingly, the relationship is not a direct proportionality but more of a quadratic one. This is not necessarily unexpected, as the role of increasing discharge current is likely two-fold here as well. In the first step, larger currents passing through the solution surface will result in greater heating and thus higher vaporization efficiency. Once in the vapor phase, greater numbers of electrons in the discharge will enhance the likelihood that atoms of analyte will become excited. As can be seen, the precision with which each of the four separate injections of analyte into the electrolyte flow is made is fairly insensitive to the discharge conditions.

Figure 2B:
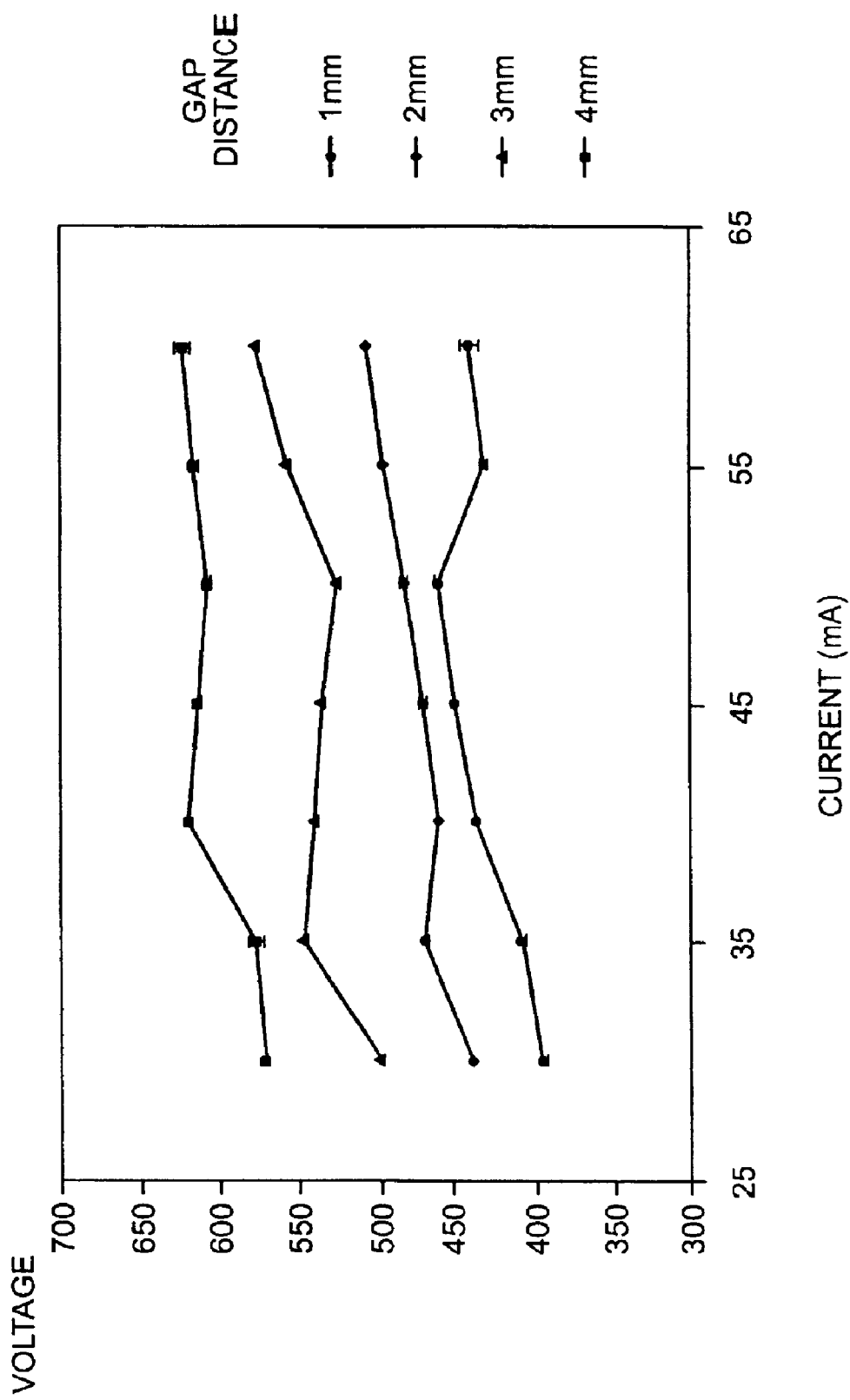
FIG. 2b is a graphic representation of the current-voltage characteristics of an embodiment of the LS-APGD for different inter-electrode gap distances at reversed polarity. Solution flow rate=1.5 mL/min., $HNO_3$:HPLC water electrolyte, pH=1.

The data presented in FIGS. 2 and 3 suggest that higher currents could be stably investigated with the aid of the flow of cooling nitrogen gas 38 dispensed from concentric cylinder 32 shown schematically in FIG. 14 for example. The flow of nitrogen gas (indicated schematically in FIGS. 13 and 14 by the arrows designated by the numeral 38) around the exterior of the discharge end 24 of the capillary 22 keeps the temperature resulting from the heat generated from the current flow at the discharge end 24 of the capillary or the copper counter electrode 34 (depending on polarity) from exceeding the melting temperature of the materials forming same.

Figure 8:
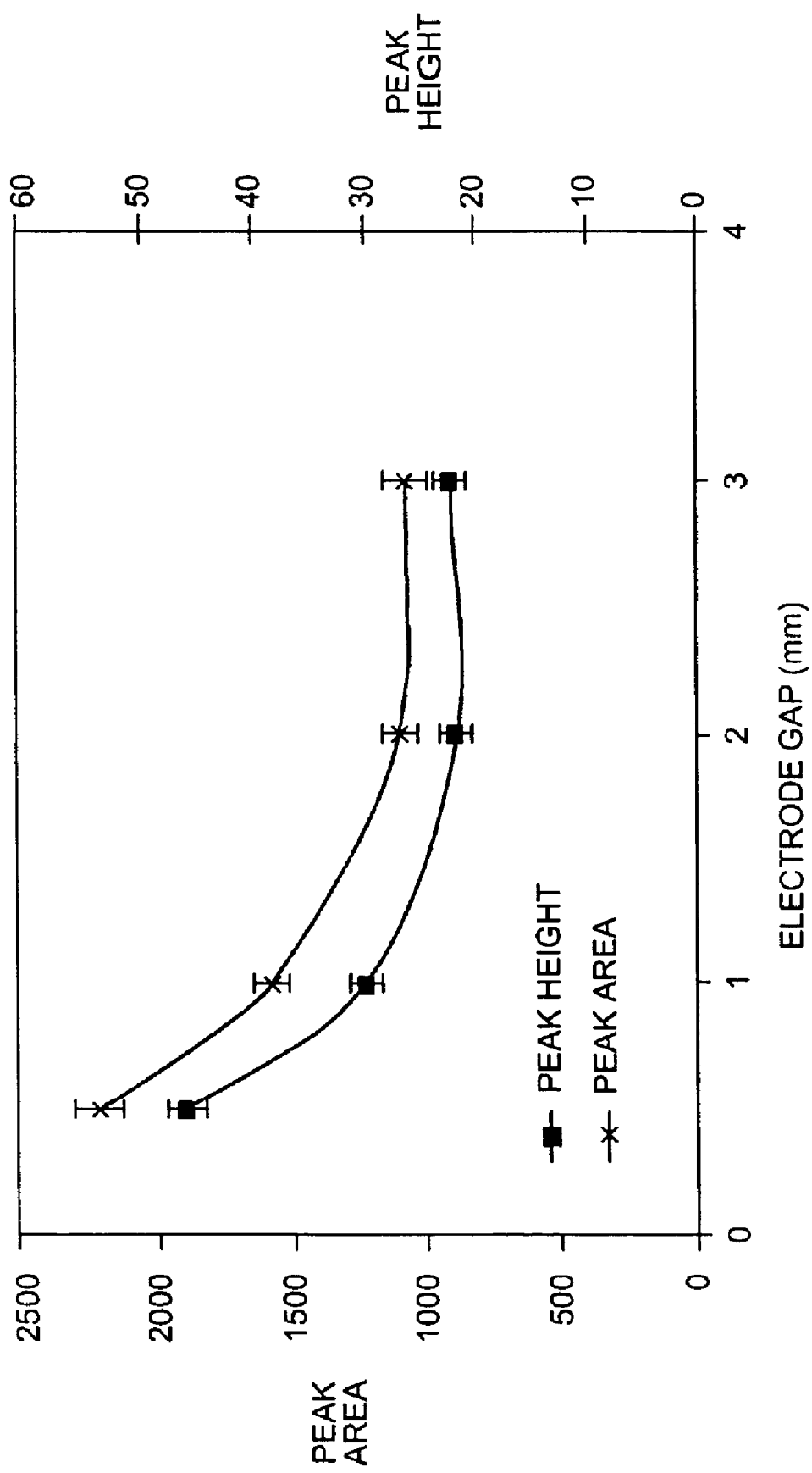
FIG. 8 is a graphic representation of the effect of inter-electrode gap on the Na (I) 589.0 nm transient peak height and area in an embodiment of the LS-APGD of the present invention. Quadruplicate injections of 5 µL aliquot of a 50 ppm Na solution. Electrolyte pH=1, flow rate=1 mL/min, discharge current=40 mA.

As was shown in FIG. 2, the inter-electrode gap in the LS-APGD device of the present invention has a definite influence on the operating parameters. The larger gap distances require higher maintenance voltages for a given discharge current. In terms of analyte responses, it is assumed that the separation distance that exists between the electrodes will play a role as well. Very simply, larger gaps yield lower current densities in the plasma and greater changes of analyte diffusion outside of the excitation volume. The responses for the Na (I) 589.0 nm emission depicted in FIG. 8 clearly illustrate what might be expected. As the gap distance is increased from 0.5 to 3 mm, there is a decrease in analyte response. It should be pointed out that the collection optics here were not focused on collecting light from any specific region of the plasma 36, and so the effect is not simply based on sampling geometry. More as expected, the photon flux from the plasma is diminished when the inter-electrode gap is increased.

In conventional glow discharge sources, the sample identity will affect the rate at which analyte species enter the discharge region and thus their analytical response (i.e., emission intensity). By analogy, the electrolyte identity may be expected to have some effect on the analyte response that is detected by the LS-APGD device of the present invention. As shown in FIGS. 4a and 4b, the identity and concentration of the aqueous cation affects the i-V characteristics. Therefore, it is likely that electrolyte composition will affect that observed optical response of dissolved analyte.

Figure 9:
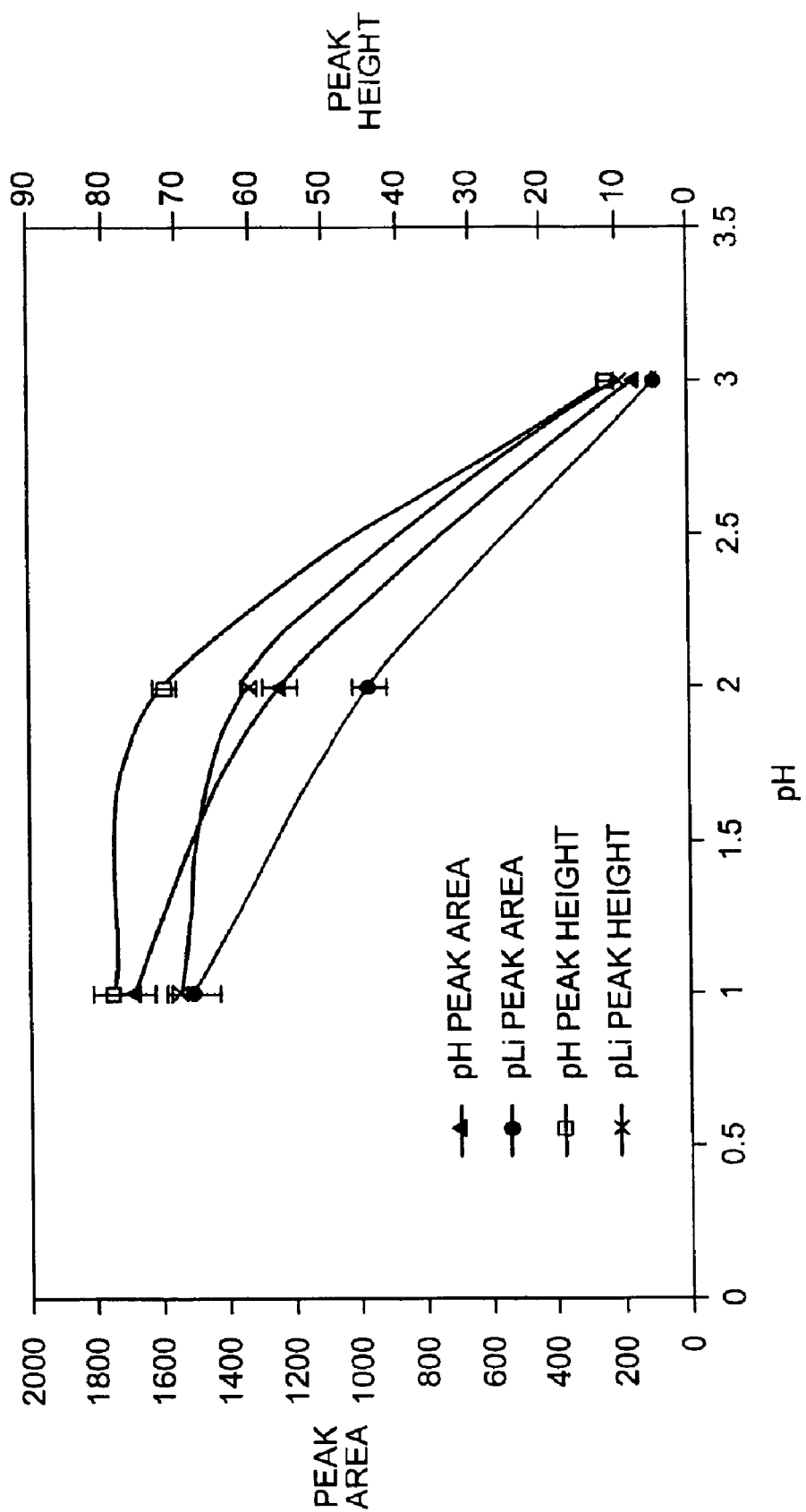
FIG. 9 is a graphic representation of the effect of pH and pLi on the Na (I) 589.0 nm transient peak height and area in an embodiment of the LS-APGD of the present invention. Quadruplicate injections of 5 µL aliquot of a 50 ppm Na solution, flow rate=1 mL/min, discharge current=40 mA, inter-electrode gap=mm.

FIG. 9 illustrates the Na (I) response to concentration for the case of hydronium and lithium ion electrolyte solutions for both the case of analyte transient peak height and analyte transient peak area. The response curves parallel each other for the two measurement modes, with the signals generated in the hydronium ion case being generally 10–15% higher than the signals generated for the Li-based solutions. The plasma was operated in a constant current mode at a value of 40 milliamperes (mA), employing a 5 µL injection of 1000 ppm Na solution into an electrolyte flow rate of 1 mL/min. Keeping in mind that the actual sample introduction method relies on a thermal vaporization step, differences in response are related to the heat generated at the electrolyte-air interface and the boiling points of the solutions. For the discharge current employed here, the differences in maintenance voltages are generally between 11 to 30%, with the H+ solutions operating higher than both the lithium and sodium solutions of equal concentration as shown in FIG. 4. As such, the higher emission responses seen here are reasonable.

Analytical Characteristics—Having developed some basis of understanding of the operation of the LS-APGD device, preliminary figures of merit were established for a range of analyte species. Analytical response curves were generated for the analytes Na, Fe, and Pb, at the respective atomic transition wavelengths of 589.0, 248.3, and 405.8 nm. The respective analytical transitions were chosen from flame-AES tabulations. FIG. 10 summarizes the analytical response curve functions that were obtained from linear least-squares fitting of emission transient peak heights and areas based on introduction of standard solutions from 50 to 1000 ppm. The electrolyte solution composition was HPLC grade water adjusted to a pH of one (1) with concentrated nitric acid, and the discharge conditions were 40 mA with a one (1) millimeter inter-electrode gap. Each data point in the calibration curves was established by taking the average value of peak height or area for four identical injections of the test solutions. In all instances, the sample-to-sample variability was less than 14% RSD, with the values being typically less than 5% RSD.

As can be seen in FIG. 10 for example, the correlation coefficients for the respective curves are routinely better for the case of peak height than for area. This reflects the variability in the tailing exhibited in FIG. 6 on a sample-to-sample basis. Limits of detection (LOD=$3 ks_{blank}/m$) for the suite of elements range from 11 to 14 ppm, with the differences between peak height and area not being appreciable for any element. These values are appreciably higher than those reported in Spectrochim. Acta 2000, 55B, pages 823 through 831 by Kim and coworkers, who obtained 0.1 to 1 ppm, though for unspecified solution volumes and integration times. Consideration of the fact that the introduced volumes that are reflected in FIG. 10 are only 5 µL, yields reasonable absolute LOD values of approximately 60 ng. In the context of use of the LS-APGD of the present invention as a low power, on-line chromatographic detector, the LOD values obtained to this point are very promising.

While a presently preferred embodiment of the invention has been described using specific terms, such description is for illustrative purposes only, and it is to be understood that changes and variations may be made without departing from the spirit or scope of the following claims.

What is claimed is:

1. A liquid sampling, atmospheric pressure, glow discharge source for the direct analysis of metals and non-metals in electrolytic solutions, comprising:

a hollow capillary having an inlet end and a discharge end opposite said inlet end;

a counter-electrode that is disposed at a predetermined distance from said discharge end of said capillary, said predetermined distance defining an electrode gap;

a first power source configured so as to maintain a glow discharge between said counter-electrode and an electrolyte solution emerging from said discharge end of said capillary; and a first mechanism connected to said capillary and configured for moving electrolytic solution through said capillary and out of said discharge end 24 at a rate in the range of at least about 1.0 microliter/min to about 2 mL/min at atmospheric pressure.

2. An apparatus as in claim 1, wherein:

said capillary having an electrically conducting element disposed between said inlet end and said discharge end and electrically communicating with the interior of said capillary, said first power source being connected between said electrically conducting element of said capillary and said counter-electrode, said first power source being configured so as to place a potential difference in the range of about 200 volts to about 1000 volts between said electrically conducting element of said capillary and said counter-electrode.

3. An apparatus as in claim 1, further comprising:

an injector connected in communication with said capillary for introducing into said capillary, a discrete amount of fluid containing at least one analyte sample of at least one material to be analyzed.

4. An apparatus as in claim 3, further comprising:
a second mechanism for separating any analytes in the electrolyte solution, said second mechanism being connected in fluid communication with said capillary downstream of said injector.

5. An apparatus as in claim 4, wherein said second mechanism for separating any analytes in the electrolyte solution includes a chromatography column.

6. An apparatus as in claim 1, wherein said first mechanism for moving electrolytic solution through said capillary and out of said discharge end includes a pump having an outlet connected in fluid communication with said inlet end of said capillary.

7. An apparatus as in claim 1, wherein said first mechanism is configured for moving electrolytic solution through said capillary and out of said discharge end at a rate in the range of at least about 1 microliter/min to about 5 mL/min at atmospheric pressure.

8. An apparatus as in claim 1, wherein said capillary defines a longitudinal axis aligned parallel to the direction of flow through said capillary, and said discharge end of said capillary is disposed such that said longitudinal axis at said discharge end is disposed generally parallel to the vertical.

9. An apparatus as in claim 8, wherein said first mechanism for moving electrolytic solution through said capillary and out of said discharge end includes a second power source having one electrical lead connected to said discharge end of said capillary and a second electrical lead connected to a point of said capillary upstream of said discharge end so as to place a potential electrical difference over the length of said capillary between said discharge end and said upstream point of said capillary.

10. An apparatus as in claim 9, wherein a single power source forms both said first power source and said second power source.

11. An apparatus as in claim 1, further comprising:
a variable resistor electrically connected between said power source and one of said electrically conducting element of said capillary and said counter-electrode.

12. An apparatus as in claim 1, wherein:
said first power source is electrically connected to said capillary so that said capillary operates as the powered electrode.

13. An apparatus as in claim 1, wherein:
said first power source is electrically connected to said counter-electrode so that said counter-electrode operates as the powered electrode.

14. An apparatus as in claim 1, wherein said first power source includes one of a direct current power source, a radio frequency power source and a microwave frequency power source.

15. An apparatus as in claim 1, further comprising:
an instrument configured for analyzing electromagnetic radiation emanating from the glow discharge; and
a light directing element disposed near said electrode gap and configured to direct electromagnetic radiation from the glow discharge to said analyzing instrument.

16. An apparatus as in claim 15, wherein said light directing element includes a fiber optic light guide.

17. An apparatus as in claim 15, wherein said analyzing instrument includes a monochromator.

18. An apparatus as in claim 1, further comprising:
an instrument configured and disposed for analyzing ionized matter emanating from said glow discharge in said electrode gap.

19. An apparatus as in claim 18, wherein said instrument includes a mass spectrometer.

20. An apparatus as in claim 1, wherein at least one of said discharge end of said capillary and said counter-electrode is fixed to a selectively movable stage.

21. An apparatus as in claim 1, wherein said capillary includes a stainless steel tube with an inside diameter of 0.254 mm and said counter-electrode is formed of copper.

22. An apparatus as in claim 1, wherein said discharge end of said capillary is formed of one of an electrically semiconducting material and an electrically insulating material.

23. An apparatus as in claim 1, further comprising:
a means for flowing gas around said discharge end of said capillary, at least a section of said gas flowing means being disposed near said discharge end of said capillary.

24. An apparatus as in claim 23, wherein said means for flowing gas around said discharge end of said capillary includes:
a gas supply conduit surrounding said discharge end of said capillary;
a supply tube connected in fluid communication with said gas supply conduit; and
a supply of gas connected in fluid communication with said supply tube.

25. A liquid sampling, atmospheric pressure, glow discharge source for the direct analysis of metals and non-metals in electrolytic solutions, comprising:
a hollow capillary having an inlet end and a discharge end opposite said inlet end, said capillary having an electrically conducting element disposed between said inlet end and said discharge end and electrically communicating with the interior of said capillary;
a means for moving electrolytic solution through said capillary and out of said discharge end at a rate in the range of at least about 1.0 microliter/min to about 5 mL/min at atmospheric pressure, said moving means being connected to said capillary;
a counter-electrode that is disposed at a predetermined distance from said discharge end of said capillary, said predetermined distance defining an electrode gap;
a first power source means for maintaining a potential difference in the range of about 200 to about 1000 volts between said electrically conducting element of said capillary and said counter-electrode and maintaining a glow discharge between said discharge end of said capillary and said counter-electrode;
a means for injecting into said capillary, a discrete amount of fluid containing a sample of at least one analyte material to be analyzed, said injecting means being connected in communication with said capillary;
a means for separating said sample into discrete volumes wherein each discrete volume being substantially composed of a single analyte, said separating means being connected in fluid communication between said injecting means and said discharge end of said capillary;
a means for flowing gas around said discharge end of said capillary, said gas flowing means including a section disposed near said discharge end of said capillary;
a means for analyzing ionized matter emanating from said glow discharge, said ion analyzing means being configured and disposed to sample ions from said glow discharge;
a means for analyzing electromagnetic radiation emanating from said glow discharge; and
a means for directing electromagnetic radiation from said glow discharge to said electromagnetic radiation analyzing means, said directing means having an input element disposed near said glow discharge.

26. A method of using a glow discharge source at atmospheric pressure for the direct analysis of metals and non-metals in electrolytic solutions, comprising:

providing a hollow capillary having an inlet end, a discharge end opposite said inlet end and an electrically conducting element disposed upstream of said discharge end and electrically communicating with the interior of said capillary;

disposing a counter-electrode spaced at a predetermined distance from said discharge end of said capillary, said space between said discharge end of said capillary and said counter-electrode defining a gap;

connecting a first power source between said electrically conducting element of said capillary and said counter-electrode so as to place a potential difference in the range of about 200 to about 1000 volts between said electrically conducting element of said capillary and said counter-electrode;

sustaining a glow discharge in said gap; and moving a flow of electrolytic solution to said discharge end of said capillary at a flow rate in the range of at least about 1.0 microliter/min to about 2 mL/min.

27. A method as in claim 26, wherein the range of said flow rate is at least about 1.0 microliter/min to about 5 mL/min.

28. A method as in claim 26, further comprising the step of:

controlling said flow rate of electrolytic solution to said discharge end of said capillary and said potential difference so as to vaporize substantially all of said electrolyte solution that reaches said discharge end of said capillary.

29. A method as in claim 26, further comprising the step of:

disposing said discharge end of said capillary so that said flow of said electrolyte solution reaches said discharge end with a vertically disposed direction of said flow of electrolyte solution.

30. A method as in claim 26, wherein said step of moving said flow of said electrolyte solution out of said discharge end of said capillary is accomplished by electro-osmotically flowing said electrolytic solution.

31. A method as in claim 30, wherein said step of electro-osmotically flowing said electrolytic solution includes the steps of connecting one electrical lead of a second power source to said discharge end of said capillary; and connecting a second lead of said second power source to a point of said capillary upstream of said discharge end so as to place a potential electrical difference over the length of said capillary between said discharge end and said upstream point of said capillary.

32. A method as in claim 26, further comprising:

injecting a discrete volume of less than about 0.5 milliliters of at least one analyte into said electrolyte solution before said electrolyte solution and said discrete volume of analyte reach said discharge end of said capillary.

33. A method as in claim 32, further comprising:

passing said discrete volume of analyte through a separation mechanism before introducing said discrete volume of analyte into said electrolyte solution that eventually reaches said discharge end of said capillary.

34. A method as in claim 32, further comprising:

passing said electrolyte solution through a separation mechanism before said electrolyte solution reaches said discharge end of said capillary.

35. A method as in claim 26, further comprising:

directing electromagnetic radiation from said glow discharge to an instrument for analyzing said directed electromagnetic radiation.

36. A method as in claim 35, wherein one of a fiber optic light guide and a monochromator is used to direct said electromagnetic radiation from said glow discharge to said instrument.

37. A method as in claim 26, further comprising:

directing ionized matter emanating from said glow discharge to an instrument for analyzing said ionized matter.

38. A method as in claim 37, wherein said instrument is a mass spectrometer.

39. A method as in claim 26, further comprising:

cooling said discharge end of said capillary while sustaining said glow discharge in said gap.

40. A method as in claim 26, further comprising:

flowing gas around said discharge end of said capillary while sustaining said glow discharge.

41. A method as in claim 40, further comprising:

directing said gas flow in the same direction as the direction of said flow of electrolyte solution that reaches said discharge end of said capillary.

42. A method as in claim 26, wherein said first power source includes one of a direct current power source, a radio frequency power source and a microwave frequency power source.

* * * * *